US007008778B1

(12) United States Patent
Ji et al.

(10) Patent No.: US 7,008,778 B1
(45) Date of Patent: Mar. 7, 2006

(54) BREAST CANCER SPECIFIC GENE 1

(75) Inventors: Hongjun Ji, San Diego, CA (US);
Craig A. Rosen, Laytonsville, MD (US)

(73) Assignee: Human Genome Sciences, Inc., Rockville, MD (US)

(*) Notice: Subject to any disclaimer, the term of this patent is extended or adjusted under 35 U.S.C. 154(b) by 0 days.

(21) Appl. No.: 09/017,715

(22) Filed: Feb. 3, 1998

Related U.S. Application Data

(60) Provisional application No. 60/037,080, filed on Feb. 3, 1997.

(51) Int. Cl.
| | |
|---|---|
| C12N 15/00 | (2006.01) |
| C12N 15/63 | (2006.01) |
| C12N 5/10 | (2006.01) |
| C12N 1/15 | (2006.01) |
| C12N 1/21 | (2006.01) |

(52) U.S. Cl. ............... 435/69.1; 435/320.1; 435/252.3; 435/254.11; 435/325; 536/23.5; 536/24.31

(58) Field of Classification Search ............... 536/23.1, 536/24.31, 23.5; 435/69.1, 320.1, 252.1, 435/325, 252.3, 254.11
See application file for complete search history.

(56) References Cited

U.S. PATENT DOCUMENTS 6,054,289 A * 4/2000 Moore ........................ 435/69.1

FOREIGN PATENT DOCUMENTS

EP          0 908 727 A1     4/1999

OTHER PUBLICATIONS

Bork, P, "Powers and Pitfalls in Sequence Analysis . . . ", Genome Research, vol. 10, pp. 398-400, 2000.*
Frisch et al, "A soluble Immunoglobulin Variable Domain without a Disulfide Bridge . . . ", Biol. Chem. Hoppe-Seyler, vol. 375, pp. 353-356, May 1994.*
Kim et al, "Restoring allosterism with compensatory mutations in hemoglobin", PNAS, vol. 91, pp. 11547-11551, Nov. 1994.*
Matthews, B., "Genetic and Structural Analysis of the Protein Stability Problem", in Perspectives in Biochemistry, Ed. Hans Neurath, vol. 1, pp. 6-9, 1989.*
Mathews and Van Holde, Biochemistry (Textbook), 2nd edition, pp. 165-171, 1996.*
Molecular Biol. of the Cell, 3rd Ed. Brace Albert, Ed. p. 40, 1996.*
A. Branch, "A hitchhiker's guide to antisense and nonantisense biochemical pathways", Hepatology, vol. 24, pp. 1517-1529.*
Broaddus et al, "Strategies for the design and delivery of antisense oligonucleotides in central nervous system", Methods in Enzymology, vol. 314, pp. 121-135.*
Burgess et al, "Possible dissociation of the heparin-binding and mitogenic activities of heparin-binding growth-factor-1 from its receptor binding activities", Journal of Cellular Biology, 1990, vol. 11, pp. 2129-2138.*
Lazar et al, "Transforming growth factor alpha", Molecular and Cellular biology, 1988, vol. 8, pp. 1247-1252.*
Accession No. AAQ61427, Mar., 1994.*
Sambrook et al, Molecular Cloning: A Laboratory Manual, 2nd Edition, 1989, pp. 10.27-10.28.*
Allred, D.C. et al., "HER-2/neu in Node-Negative Breast Cancer: Prognostic Significance of Overexpression Influenced by the Presence of In Situ Carcinoma," J. Clin. Oncol. 10(4):599-605 (Apr. 1992).
Angerer, L.M. and Angerer, R.C., "In situ hybridization to cellular RNA with radiolabelled RNA probes," in: In situ hybridization: a practical approach, Wilkinson, D.G., Ed., IRL Press at Oxford University Press, Oxford University Press, Oxford and New York; pp. 15-32 (1992).
Bergh, J. et al., "Complete sequencing of the p53 gene provides prognostic information in breast cancer patients, particularly in relation to adjuvant systemic therapy and radiotherapy," Nature Med. 1(10):1029-1034 (Oct. 1995).
Chen, Z. and Sager, R., "Differential Expression Human Tissue Factor in Normal Mammary Epithelial Cells and in Carcinomas," Mol. Med. 1(2):153-160 (Jan. 1995).
Elledge, R.M. et al., "The role and prognostic significance of p53 gene alterations in breast cancer," Breast Cancer Res. Treatment 27(1/2):95-102 (Jul./Aug. 1993).
Ernster, V.L. et al., "Incidence of and Treatment for Ductal Carcinoma In Situ of the Breast," JAMA 275(12):913-918 (Mar. 1996).
Fernö, M. et al., "Cathepsin D, Both a Prognostic Factor and a Predictive Factor for the Effect of Adjuvant Tamoxifen in Breast Cancer," Eur. J. Cancer 30A(14):2042-2048 (Dec. 1994).
Foekens, J.A. et al., "Urokinase-Type Plasminogen Activator and Its Inhibitor PAI-1: Predictors of Poor Response to Tamoxifen Therapy in Recurrent Breast Cancer," J. Natl. Cancer Inst. 87(10):751-756 (May 1995).
Futreal, P.A. et al., "BRCA1 Mutations in Primary Breast and Ovarian Carcinomas," Science 266:120-122 (Oct. 1994).
Gasparini, G. et al., "Evaluating the Potential Usefulness of New Prognostic and Predictive Indicators in Node-Negative Breast Cancer Patients," J. Natl. Cancer Inst. 85(15):1206-1219 (Aug. 1993).

(Continued)

Primary Examiner—Karen A. Canella
(74) Attorney, Agent, or Firm—Human Genome Sciences, Inc.

(57) ABSTRACT

The present invention relates to a novel BCSG1 protein. In particular, isolated nucleic acid molecules are provided encoding the human BCSG1 protein. BCSG1 polypeptides are also provided as are vectors, host cells and recombinant methods for producing the same. Also provided are diagnostic methods for detecting breast cancer.

48 Claims, 4 Drawing Sheets

OTHER PUBLICATIONS

Gasparini, G. et al., *Erratum:* "Evaluating the Potential Usefulness of New Prognostic and Predictive Indicators in Node-Negative Breast Cancer Patients," *J. Natl. Cancer Inst.* 85(19):1605 (Oct. 1993).

Goldhirsch, A. et al., "Meeting Highlights: International Consensus Panel on the Treatment of Primary Breast Cancer," *J. Natl. Cancer Inst.* 87(19):1441-1445 (Oct. 1995).

Gusterson, B.A. et al., "Prognostic Importance of c-*erb*B-2 Expression in Breast Cancer," *J. Clin. Oncol.* 10(7):1049-1056 (Jul. 1992).

Harris, A.L. et al., "Breast Cancer Angiogenesis: Therapy Target and Prognostic Factor," *Eur. J. Cancer* 31A(5):831-832 (Jun. 1995).

Klijn, J.G.M. et al., "Prognostic Factors and Response to Therapy in Breast Cancer," *Cancer Surveys* 18:165-198 (1993).

Liang, P. et al., "Differential Display and Cloning of Messenger RNAs from Human Breast Cancer *versus* Mammary Epithelial Cells," *Cancer Res.* 52(24):6966-6968 (Dec. 1992).

Manning, D.L. et al., "Differential Expression of Oestrogen Regulated Genes in Breast Cancer," *Acta Oncologica* 35(5): 641-646 (1995). Presented at the 5th Scandinavian Breast Cancer Symposium, Reykjavik, Iceland, May-Jun. 1994.

Miki, Y. et al., "A Strong Candidate for the Breast and Ovarian Cancer Susceptibility Gene *BRCA1*," *Science* 266: 66-71 (Oct. 1994).

Porter-Jordan, K. and Lippman, M.E., "Overview of the Biologic Markers of Breast Cancer," *Hematol. Oncol. Clin. North Am.* 8(1):73-100 (Feb. 1994).

Sager, R. et al., "Identification by differential display of alpha 6 integrin as a candidate tumor suppressor gene," *FASEB J.* 7(10):964-970 (Jul. 1993).

Schena, M. et al., "Quantitative Monitoring of Gene Expression Patterns with a Complementary DNA Microarray," *Science* 270:467-470 (Oct. 1995).

Steeg, P.S. et al., "*Nm23* and breast cancer metastasis," *Breast Cancer Res. Treatment* 25(2):175-187 (Feb. 1993).

Velculescu, V.E. et al., "Serial Analysis of Gene Expression," *Science* 270:484-487 (Oct. 1995).

Watson, M.A. and Fleming, T.P., "Isolation of Differentially Expressed Sequence Tags from Human Breast Cancer," *Cancer Res.* 54(17):4598-4602 (Sep. 1994).

Wooster, R. et al., "Localization of a Breast Cancer Susceptibility Gene, *BRCA2*, to Chromosome 13q12-13," *Science* 265:2088-2090 (Sep. 1994).

Zhang, M. et al., "Differential Expression of Elafin in Human Normal Mammary Epithelial Cells and Carcinomas Is Regulated at the Transcriptional Level," *Cancer Res.* 55(120):2537-2541 (Jun. 1995).

Zou, Z. et al., "Maspin, a Serpin with Tumor-Supressing Activity in Human Mammary Epithelial Cells," *Science* 263:526-529 (Jan. 1994).

Donohue, S.J., et al., "Human Hydroxyindole-0-Methyltransferase: presence of LINE-1 Fragment in a cDNA Clone and Pineal mRNA," *DNA and Cell Biology* 12:715-727, Mary Ann Liebert, Inc. Publishers (1993).

NCBI Entrez, GenBank Report, Accession No. M83779, from Donohue, S.J., et al. (1993).

Hayes et al. "Tumor markers for breast cancer: current utilities and future prospects", *Hematology/Oncology Clinics of North America* 8(3):485-506 (1994).

Ji et al. "Identification of a breast cancer-specific gene, BCSG1, by direct differential cDNA sequencing", *Cancer Research* 57(4):759-764 (1997).

Lavedan et al. "Identification, localization and characterization of the human gamma-synuclein gene", *Human Genetics* 103(1):106-112 (1998).

Lu et al. "Molecular mechanisms for aberrant expression of the human breast cancer specific gene 1 in breast cancer cells: control of transcription by DNA methylation and intronic sequences", *Oncogene* 20(37):5173-5185 (2001).

Wu et al. "Stage-specific expression of breast cancer-specific gene gamma-synuclein", *Cancer Epidemiology, Biomarkers and Prevention* 12(9):920-925 (2003).

European Search Report, Application No. 04 01 4241, dated Dec. 6, 2004.

* cited by examiner

Figure 1

```
         10                30                50
CACGAGCCACCATGGATGTTTTCAAGAAGGGCTTCTCCATCGCCAAGAAGGGCGTGGTGG
             M  D  V  F  K  K  G  F  S  I  A  K  K  G  V  V  G 70                90               110
GTGCGGTGGAAAAGACCAAGCAGGGGGTGACGGAAGCAGCTGAGAAGACCAAGGAGGGGG
 A  V  E  K  T  K  Q  G  V  T  E  A  A  E  K  T  K  E  G  V 130               150               170
TCATGTATGTGGGAGCCAAGACCAAGGAGAATGTTGTACAGAGCGTGACCTCAGTGGCCG
  M  Y  V  G  A  K  T  K  E  N  V  V  Q  S  V  T  S  V  A  E 190               210               230
AGAAGACCAAGGAGCAGGCCAACGCCGTGAGCAAGGCTGTGGTGAGCAGCGTCAACACTG
  K  T  K  E  Q  A  N  A  V  S  K  A  V  V  S  S  V  N  T  V 250               270               290
TGGCCACCAAGACCGTGGAGGAGGCGGAGAACATCGCGGTCACCTCCGGGGTGGTGCGCA
  A  T  K  T  V  E  E  A  E  N  I  A  V  T  S  G  V  V  R  K 310               330               350
AGGAGGACTTGAGGCCATCTGCCCCCCAACAGGAGGGTGAGGCATCCAAAGAGAAAGAGG
  E  D  L  R  P  S  A  P  Q  Q  E  G  E  A  S  K  E  K  E  E 370               390               410
AAGTGGCAGAGGAGGCCCAGAGTGGGGGAGACTAGAGGGCTACAGGCCAGCGTGGATGAC
  V  A  E  E  A  Q  S  G  G  D  *

430               450               470
CTGAAGAGCGCTCCTCTGCCTTGGACACCATCCCCTCCTAGCACAAGGAGTGCCCGCCTT 490               510               530
GAGTGACATGCGGGTGCCCACGCTCCTGCCCTCGTCTCCCTGGACACCCTTGGCCTGTCC

550
ACCTGTGCTG
```

Figure 4

1 AAGCTT AAAAAACTGCAAAAAATAGT TGACTT GTCAGCTGAAAACAT

Operator 1
−35

−10
50 TAAGAT GTACCCAT TGTAGCGCGATAAAAT TCACACATTAA

Operator 2

S/D
94 A AGGAGA AAATTA CATATG

BREAST CANCER SPECIFIC GENE 1

The present application claims the benefit of provisional application 60/037,080, filed Feb. 3, 1997, which is herein incorporated by reference.

FIELD OF THE INVENTION

The present invention relates to a novel breast cancer specific marker. More specifically, isolated nucleic acid molecules are provided encoding a human breast cancer specific gene 1 (BCSG1). BCSG1 polypeptides are also provided, as are vectors, host cells and recombinant methods for producing the same. Also provided are diagnostic methods for detecting breast cancer. The invention further provides an isolated BCSG1 polypeptide having an amino acid sequence encoded by a polynucleotide described herein.

RELATED ART

More than 190,000 new cases of breast cancer are diagnosed in the United States every year, with incidence increasing by approximately 1% annually (Goldhirsch, A., *JNCI* 97:1141–1145 (1995); Emster, V. L., et al., *JAMA* 275:913–918 (1996)). Studies linked to the discovery of new genetic markers and additional risk factors could provide new information that fits into the complex patient management issues surrounding breast cancer. Many new prognostic and predictive factors have been proposed and studied for breast cancer. HER 2/neu positive tumors respond poorly to endocrine treatment (Allred D. C., et al., *J. Clin Oncol.* 10:599–605 (1992); Gusterson B. A., et al., *J. Clin Oncol.* 10:1049–56 (1992)). p53 alteration has an indication of poorer prognosis and poor response to tamoxifen (Bergh J., et al., *Nature Medicine* 10: 1029–34 (1995); Elledge R. M., et al., *Breast Cancer Res Treat* 27:95–102 (1993)). The lack of Nm23 expression has an indicative value of metastatic potential and poor prognosis in invasive ductal carcinoma (Steeg P. S., et al., *Breast Cancer Res Treat* 25:175–87 (1993)). Cathepsin D, a protease suggested to have a role in breast cancer, appears to affect the potential for invasive growth (Velculescu, V. E., et al., *Science* 270:484–7 (1995); Schena, M., et al., *Science* 270:467–70 (1995); M. L. Angerer & R. C. Angerer, In: *In situ hybridization*, D. Rickwood and B. D. Hames (ed.). London: LRL Press., (1992), pp. 15–32; Ferno M., et al., *Eur J. Cancer* 30A: 2042–8 (1994)). Positive immunostaining of tumor sections with Factor VIII antibodies seems to be a marker for angiogenesis (Klijn J. G. M., et al., *Breast Cancer* 18:165–98 (1993); Harris A. L., et al., *Eur J. Cancer* 31A:831–2 (1995); Gasparini G., et al., *JNCI* 85:1206–19 (1993) (errata *JNCI* 85:1605 (1993))). It has been postulated that these tumors are targets for anti-angiogenesis drug treatment. Expression of the mdr-1 gene is proposed to be an indicator of multidrug resistance (Harris A. L., et al., *Eur J. Cancer* 31A:831–2 (1995); Gasparini G., et al., *JNCI* 85:1206–19 (1993) (errata *JNCI* 85:1605 (1993))). Poor response to endocrine therapy has been indicated for uPA/PAI-1, a plasminogen activator/inhibitor (Foekens J. A., et al., *JNCI* 87:751–6 (1995)). Also receiving major attention are the familial breast cancer related genes, BRCA1 and BRCA2 (Miki, Y., et al., *Science* 266:66–71 (1994); Wooster, R., et al., *Science* 265:2088–2090 (1994); Futreal, P. A., et al., *Science* 266:120–122 (1994)).

Thus, the onset and progression of breast cancer is accompanied by multiple genetic changes that result in qualitative and quantitative alterations in individual gene expression (Porter-Jordan, K. & Lippman, M. E., Hematol. *Oncol. Clin. N. Am.* 8:73–100 (1994)). Many of these quantitative genetic changes may manifest themselves as alterations in the cellular complement of novel transcribed mRNAs. Identification of these mRNAs could provide clinically useful information for patient management and prognosis while enhancing our understanding of breast cancer pathogenesis.

Identification of quantitative changes in gene expression that occur in the malignant mammary gland may yield novel molecular markers which may be useful in the diagnosis and treatment of human breast cancer. Several differential cloning methods, such as differential display polymerase chain reaction and subtractive hybridization, have been used to identify the genes differentially expressed in breast cancer biopsies, as compared to normal breast tissue controls (Watson, M. A. & Fleming, T. P., *Cancer Res.* 54:4598–4602 (1994); Sager, R., et al., *FASEB J.* 7:964–970 (1993); Chen, Z. & Sager, R., *Mol. Med.* 1:153–160 (1995); Zhang, M., et al., *Cancer Res.* 55:2537–2541 (1995); Zou, Z., et al., *Science* 263:526–529)). However, these investigations have involved the relatively time- and labor-intensive steps of subcloning, library screening, and cDNA sequencing of individual genes (Sager, R., et al., *FASEB J.* 7:964–970 (1993); Liang, P., et al., *Cancer Res.* 52:6966–6968 (1992)).

Although pathological endpoints such as tumor size, lymph node status and status of estrogen receptor and progesterone receptor remain the most useful guides in prognosis and selecting treatment strategies for breast cancer (Manning, D. L., et al., *Acta Oncol.* 34:641–646 (1995)), there is still a need to further investigate the molecular mechanisms that determine the properties of an individual tumor e.g., probability of metastasis. While numerous prognostic factors have been identified, few have contributed to defining clinical response to therapy.

SUMMARY OF THE INVENTION

The present invention provides isolated nucleic acid molecules comprising a polynucleotide encoding the BCSG1 polypeptide having the amino acid sequence shown in FIG. 1 (SEQ ID NO:2) or the amino acid sequence encoded by the cDNA clones deposited in a bacterial host as ATCC Deposit Number 97175 on Jun. 2, 1995 or as ATCC Deposit Number 97856 on Jan. 23, 1997.

The present invention also relates to recombinant vectors, which include the isolated nucleic acid molecules of the present invention, and to host cells containing the recombinant vectors, as well as to methods of making such vectors and host cells and for using them for production of BCSG1 polypeptides or peptides by recombinant techniques.

In accordance with another aspect of the present invention, there is provided a method of and products for diagnosing breast cancer metastases by detecting an altered level of a polypeptide corresponding to the breast specific genes of the present invention in a sample derived from a host, whereby an elevated level of the polypeptide indicates a breast cancer diagnosis.

The present invention further relates to antibodies specific to the polypeptides of the present invention, which may be employed to detect breast cancer cells or breast cancer metastasis.

The polynucleotides and polypeptides described herein are useful as markers for breast cancer.

BRIEF DESCRIPTION OF THE FIGURES

FIG. 1 shows the nucleotide (SEQ ID NO:1) and deduced amino acid (SEQ ID NO:2) sequences of BCSG1. The protein has a deduced molecular weight of about 14.2 kDa. The predicted amino acid sequence of the BCSG1 protein is also shown.

FIG. 4 shows the nucleotide sequence of the regulatory elements of the pHE promoter (SEQ ID NO:11). The two lac operator sequences, the Shine-Delgarno sequence (S/D), and the terminal HindIII and NdeI restriction sites (italicized) are indicated.

DETAILED DESCRIPTION

Figure 2:
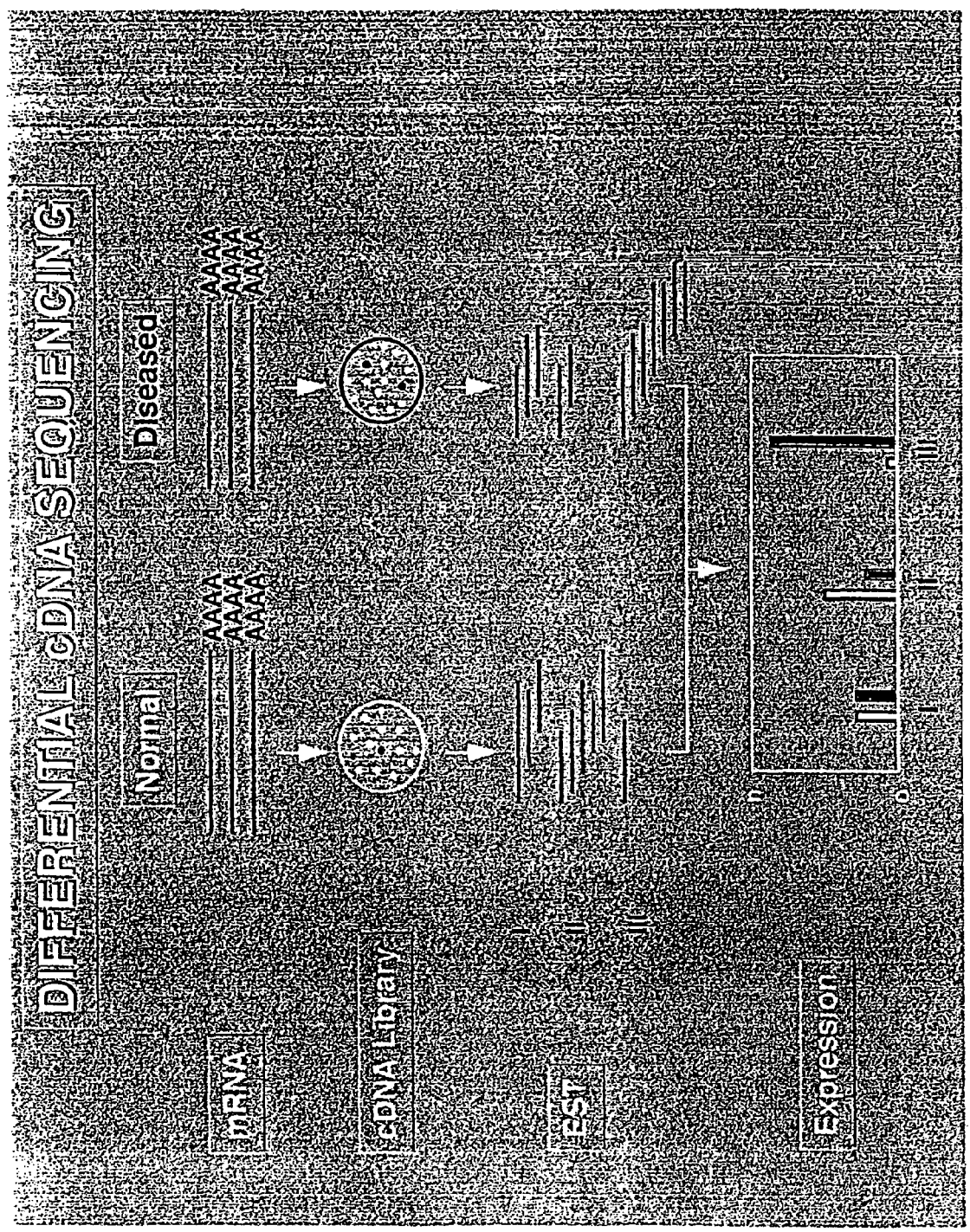
FIG. 2 shows the differential cDNA sequencing approach. Messenger RNAs from normal and diseased tissues were extracted and used for making the cDNA libraries. These libraries are searched by EST method involving automated DNA sequence analysis of randomly selected cDNA clones. The ESTs with overlapping sequences were grouped into unique EST groups. Each unique EST group, which does not overlap to each other in sequence, was analyzed for its relative expression by examining the number of expressed individual EST in the libraries of normal vs diseased tissues. Three EST groups are listed. Blue EST group represents gene that is equally expressed in both libraries. Green EST group represents gene that is more expressed in normal library compared to diseased library. Red EST group represent gene that is more expressed in diseased library compared to normal library.

The present invention provides isolated nucleic acid molecules comprising a polynucleotide encoding a BCSG1 polypeptide having the amino acid sequence shown in FIG. 1 (SEQ ID NO:2), which was determined by sequencing a cloned cDNA. The BCSG1 protein of the present invention shares sequence homology with human AD amyloid. The nucleotide sequence shown in FIG. 1 (SEQ ID NO:1) was obtained by sequencing the 184,497 clone, which as deposited on Jan. 23, 1997 at the American Type Culture Collection, Patent Depository, 10801 University Boulevard, Manassas, Va. 20110-2209; and given accession number 97856. The deposited clone is contained in the pBluescript SK(-) plasmid (Stratagene, La Jolla, Calif.). The BSCG-1 gene was also deposited on Jun. 2, 1995 at the American Type Culture Collection, 12301 Parklawn Drive, Rockville, Md. 20852, and given accession number 97175.

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIG. 1, a nucleic acid molecule of the present invention encoding a BCSG1 polypeptide may be obtained using standard cloning and screening procedures, such as those for cloning cDNAs using mRNA as starting material. Illustrative of the invention, the nucleic acid molecule described in FIG. 1 (SEQ ID NO:1) was discovered in a cDNA library derived from breast cancer. The gene was also identified in cDNA libraries from brain tissue. The determined nucleotide sequence of the BCSG1 cDNA of FIG. 1 (SEQ ID NO:1) contains an open reading frame encoding a protein of 127 amino acid residues, with an initiation codon at positions 12–14 of the nucleotide sequence in FIG. 1 (SEQ ID NO:1), and a deduced molecular weight of about 14.2 kDa. The BCSG1 protein shown in FIG. 1 (SEQ ID NO:2) is about 54% identical to non-Aβ fragment of human Alzheimer's disease (AD) amyloid protein.

As one of ordinary skill would appreciate, due to the possibilities of sequencing errors, the predicted BCSG1 polypeptide encoded by the deposited cDNA comprises about 127 amino acids, but may be anywhere in the range of 110–140 amino acids.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) shown in FIG. 1 (SEQ ID NO:1) and DNA molecules which comprise a sequence substantially different from those described above but which, due to the degeneracy of the genetic code, still encode the BCSG1 protein. Of course, the genetic code is well known in the art. Thus, it would be routine for one skilled in the art to generate such degenerate variants. SEQ ID NO:12 is a full length cDNA sequence of breast specific gene 1 of the present invention.

In another aspect, the invention provides isolated nucleic acid molecules encoding the BCSG1 polypeptide having an amino acid sequence encoded by the cDNA clone contained in the plasmid deposited as ATCC Deposit No. 97856 on Jan. 23, 1997 or contained in the plasmid deposited as ATCC Deposit No. 97175 on Jun. 2, 1995. The invention further provides an isolated nucleic acid molecule having the nucleotide sequence shown in FIG. 1 (SEQ ID NO:1) or the nucleotide sequence of the BCSG1 cDNA contained in the above-described deposited clone, the full-length BCSG1 polypeptide lacking the N-terminal methionine or a nucleic acid molecule having a sequence complementary to one of the above sequences. Such isolated molecules, particularly DNA molecules, are useful as probes for gene mapping, by in situ hybridization with chromosomes, and for detecting expression of the BCSG1 gene in human tissue, for instance, by Northern blot analysis.

The present invention is further directed to fragments of the isolated nucleic acid molecules described herein. By a fragment of an isolated nucleic acid molecule having the nucleotide sequence of the deposited cDNA or the nucleotide sequence shown in FIG. 1 (SEQ ID NO:1) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50, 75, 100, 125, 150, 175, 200, 225, 250, 275, 300, 325, 350, 375, 400, 425, 450, 475, 500, 525, 550 nt in length are also useful according to the present invention as are fragments corresponding to most, if not all, of the nucleotide sequence of the deposited cDNA or as shown in FIG. 1 (SEQ ID NO:1). By a fragment at least 20 nt in length, for example, is intended fragments which include 20 or more contiguous bases from the nucleotide sequence of the deposited cDNA or the nucleotide sequence as shown in FIG. 1 (SEQ ID NO:1).

Preferred nucleic acid fragments of the present invention include nucleic acid molecules encoding epitope-bearing portions of the BCSG1 protein. In particular, such nucleic acid fragments of the present invention include nucleic acid molecules encoding: a polypeptide comprising amino acid residues from about 94 to about 107 in FIG. 1 (SEQ ID NO:2); a polypeptide comprising amino acid residues from about 120 to about 127 in FIG. 1 (SEQ ID NO:2). The inventors have determined that the above polypeptide fragments are antigenic regions of the BCSG1 protein. Methods for determining other such epitope-bearing portions of the BCSG1 protein are described in detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clones contained in ATCC Deposits 97856 or 97175. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5× Denhardt's solution, 10% dextran sulfate, and 20 mg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIG. 1 (SEQ ID NO:1)). Of course, a polynucleotide which hybridizes only to a poly A sequence (such as the 3' terminal poly(A) tract of the BCSG1 cDNA shown in FIG. 1 (SEQ ID NO:1)), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a BCSG1 polypeptide may include those encoding the amino acid sequence of the polypeptide, by itself; the coding sequence for the polypeptide and additional sequences, such as those encoding an amino acid leader or secretory sequence, such as a pre-, or pro- or prepro-protein sequence; the coding sequence of the polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the BCSG1 fused to Fc at the N- or C-terminus.

The present invention further relates to variants of the nucleic acid molecules of the present invention, which encode portions, analogs or derivatives of the BCSG1 protein. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the BCSG1 protein or portions thereof. Also especially preferred in this regard are conservative substitutions.

Further embodiments of the invention include isolated nucleic acid molecules comprising a polynucleotide having a nucleotide sequence at least 90% identical, and more preferably at least 95%, 96%, 97%, 98% or 99% identical to (a) a nucleotide sequence encoding the BCSG1 polypeptide having the amino acid sequence in FIG. 1 (SEQ ID NO:2); (b) a nucleotide sequence encoding the polypeptide having the amino acid sequence in SEQ ID NO:2, but lacking the N-terminal methionine; (c) a nucleotide sequence encoding the BCSG1 polypeptide having the amino acid sequence encoded by the cDNA clones contained in ATCC Deposit Nos. 97856 or 97175; or (d) a nucleotide sequence complementary to any of the nucleotide sequences in (a), (b) or (c).

By a polynucleotide having a nucleotide sequence at least, for example, 95% "identical" to a reference nucleotide sequence encoding a BCSG1 polypeptide is intended that the nucleotide sequence of the polynucleotide is identical to the reference sequence except that the polynucleotide sequence may include up to five point mutations per each 100 nucleotides of the reference nucleotide sequence encoding the BCSG1 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIG. 1 (SEQ ID NO:1) or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, *Advances in Applied Mathematics* 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90%, 95%, 96%, 97%, 98% or 99% identical to the nucleic acid sequence shown in FIG. 1 (SEQ ID NO:1) or to the nucleic acid sequence of the deposited cDNA, irrespective of whether they encode a polypeptide having BCSG1 activity. This is because even where a particular nucleic acid molecule does not encode a polypeptide having BCSG1 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having BCSG1 activity include, inter alia, (1) isolating the BCSG1 gene or allelic variants thereof in a cDNA library; (2) in situ hybridization (e.g., "FISH") to metaphase chromosomal spreads to provide precise chromosomal location of the BCSG1 gene, as described in Verma et al., *Human Chromosomes: A Manual of Basic Techniques*, Pergamon Press, New York (1988); and Northern Blot analysis for detecting BCSG1 mRNA expression in specific tissues.

Preferred, however, are nucleic acid molecules having sequences at least 90%, 95%, 96%, 97%, 98% or 99% identical to the nucleic acid sequence shown in FIG. 1 (SEQ ID NO:1) or to the nucleic acid sequence of the deposited cDNA which do, in fact, encode a polypeptide having BCSG1 protein activity. By "a polypeptide having BCSG1 activity" is intended polypeptides exhibiting activity similar, but not necessarily identical, to an activity of the BCSG1 protein of the invention, as measured in a particular biological assay. BCSG1 protein is believed to be involved with apoptosis. BCSG1 protein activity can be measured using assays that measure apoptosis. For example, human breast cancer cells cultured on Lab-Tek chamber slides (Nunc, Inc.) are treated with or without recombinant BCSG1 protein or a candidate BCSG1 protein. The cells are then treated with several concentrations of an apoptotic inducer, such as adriamycin. Apoptosis is compared between the treated and control cells where DNA fragmentation is the criteria for apoptotic death using the following assay. At various time points after the adriamycin treatment, adherent cells are stained with DNA-specific fluorochrome diamino-2 phenylindole (Boehringer Mannheim) in a 1 $\mu$g/ml methanol solution. Cells are counted within 20 minutes of staining on a Zeiss Axiophot epiflouresence microscope. Experiments are performed in triplicate with at least 150 cells scored at each point. Fragmented or condensed nuclei are scored as apoptotic. Intact or mitotic nuclei are scored as normal.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIG. 1 (SEQ ID NO:1) will encode a polypeptide "having BCSG1 protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having BCSG1 protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that proteins are surprisingly tolerant of amino acid substitutions.

Vectors and Host Cells

The present invention also relates to vectors which include the isolated DNA molecules of the present invention, host cells which are genetically engineered with the recombinant vectors, and the production of BCSG1 polypeptides or fragments thereof by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the E. coli lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Appropriate culture mediums and conditions for the above-described host cells are known in the art.

In addition to the use of expression vectors in the practice of the present invention, the present invention further includes novel expression vectors comprising operator and promoter elements operatively linked to nucleotide sequences encoding a protein of interest. One example of such a vector is pHE4-5 which is described in detail below.

Figure 3:
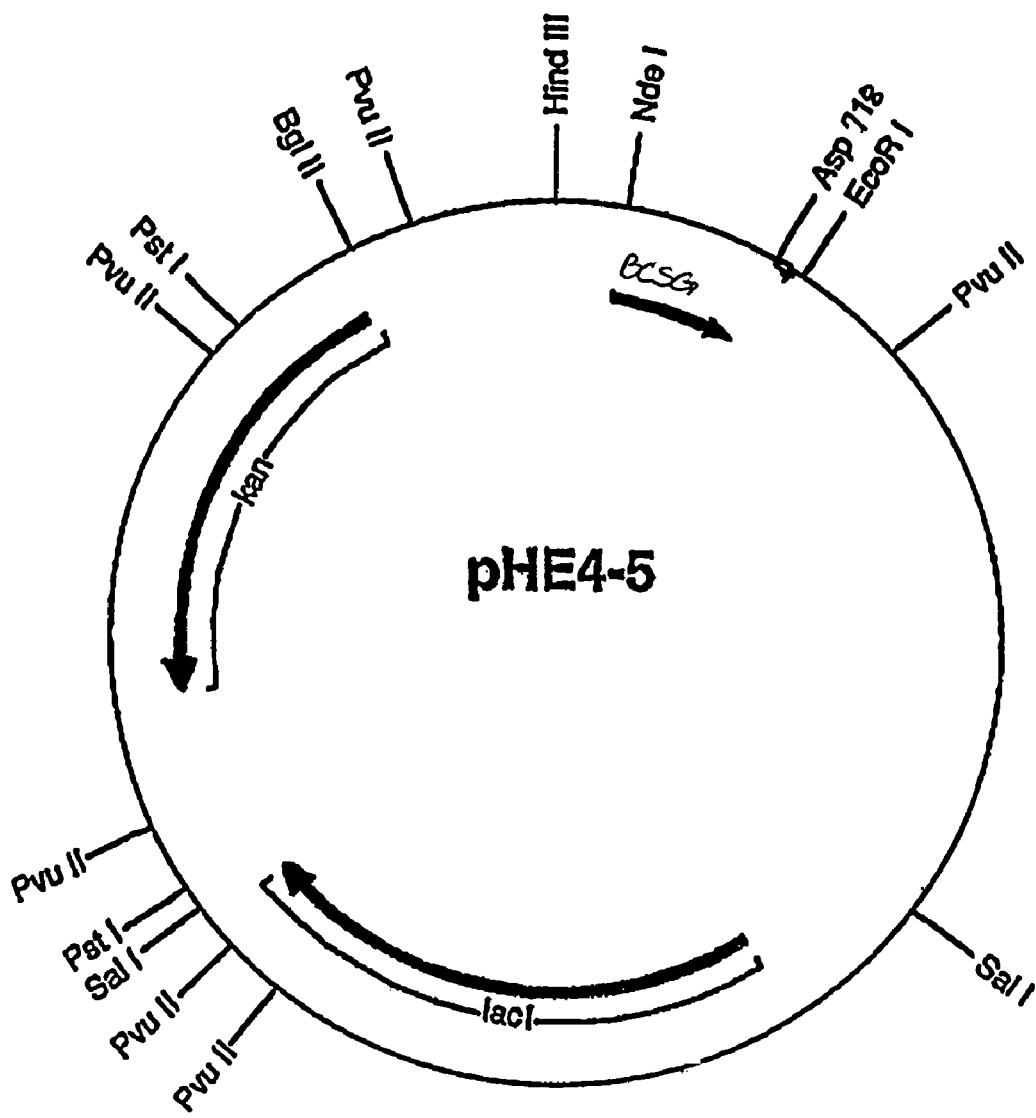
FIG. 3 shows a schematic representation of the pHE4-5 expression vector (SEQ ID NO:10) and the subcloned BSCG-1 cDNA coding sequence. The locations of the kanamycin resistance marker gene, the BSCG-1 coding sequence, the oriC sequence, and the lacIq coding sequence are indicated.

As summarized in FIGS. 3 and 4, components of the pHE4-5 vector (SEQ ID NO:10) include: 1) a neomycinphosphotransferase gene as a selection marker, 2) an E. coli origin of replication, 3) a T5 phage promoter sequence, 4) two lac operator sequences, 5) a Shine-Delgarno sequence, 6) the lactose operon repressor gene (lacIq). The origin of replication (oriC) is derived from pUC19 (LTI, Gaithersburg, Md.). The promoter sequence and operator sequences were made synthetically. Synthetic production of nucleic acid sequences is well known in the art. CLONTECH 95/96 Catalog, pages 215–216, CLONTECH, 1020 East Meadow Circle, Palo Alto, Calif. 94303. A nucleotide sequence encoding BCSG-1 (SEQ ID NO:1), is operatively linked to the promoter and operator by inserting the nucleotide sequence between the NdeI and Asp718 sites of the pHE4-5 vector.

As noted above, the pHE4-5 vector contains a lacIq gene. LacIq is an allele of the lacI gene which confers tight regulation of the lac operator. Amann, E. et al., Gene 69:301–315 (1988); Stark, M., Gene 51:255–267 (1987). The lacIq gene encodes a repressor protein which binds to lac operator sequences and blocks transcription of downstream (i.e., 3') sequences. However, the lacIq gene product dissociates from the lac operator in the presence of either lactose or certain lactose analogs, e.g., isopropyl B-D-thiogalactopyranoside (IPTG). BSCG-1 thus is not produced in appreciable quantities in uninduced host cells containing the pHE4-5 vector. Induction of these host cells by the addition of an agent such as IPTG, however, results in the expression of the BSCG-1 coding sequence.

The promoter/operator sequences of the pHE4-5 vector (SEQ ID NO:11) comprise a T5 phage promoter and two lac operator sequences. One operator is located 5' to the transcriptional start site and the other is located 3' to the same site. These operators, when present in combination with the lacIq gene product, confer tight repression of down-stream sequences in the absence of a lac operon inducer, e.g., IPTG. Expression of operatively linked sequences located downstream from the lac operators may be induced by the addition of a lac operon inducer, such as IPTG. Binding of a lac inducer to the lacIq proteins results in their release from the lac operator sequences and the initiation of transcription of operatively linked sequences. Lac operon regulation of gene expression is reviewed in Devlin, T., TEXTBOOK OF BIOCHEMISTRY WITH CLINICAL CORRELATIONS, 4th Edition-(1997), pages 802–807.

The pHE4 series of vectors contain all of the components of the pHE4-5 vector except for the BSCG-1 coding sequence. Features of the pHE4 vectors include optimized synthetic T5 phage promoter, lac operator, and Shine-Delagarno sequences. Further, these sequences are also optimally spaced so that expression of an inserted gene may be tightly regulated and high level of expression occurs upon induction.

Among known bacterial promoters suitable for use in the production of proteins of the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metallothionein-I promoter.

The pHE4-5 vector also contains a Shine-Delgarno sequence 5' to the AUG initiation codon. Shine-Delgarno sequences are short sequences generally located about 10 nucleotides up-stream (i.e., 5') from the AUG initiation codon. These sequences essentially direct prokaryotic ribosomes to the AUG initiation codon.

Thus, the present invention is also directed to expression vector useful for the production of the proteins of the present invention. This aspect of the invention is exemplified by the pHE4-5 vector (SEQ ID NO:10).

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5-receptor has been fused with Fc portions for the purpose of high-throughput screening assays to identify antagonists of hIL-5. See, D. Bennett et al., *Journal of Molecular Recognition*, Vol. 8:52–58 (1995) and K. Johanson et al., *The Journal of Biological Chemistry*, Vol. 270, No. 16:9459–9471 (1995).

The BCSG1 protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

BCSG1 Polypeptides and Fragments

The invention further provides an isolated BCSG1 polypeptide having the amino acid sequence encoded by the deposited cDNA clones, or the amino acid sequence in FIG. 1 (SEQ ID NO:2), or a peptide or polypeptide comprising a portion of the above polypeptides.

It will be recognized in the art that some amino acid sequences of the BCSG1 polypeptide can be varied without significant effect of the structure or function of the protein. If such differences in sequence are contemplated, it should be remembered that there will be critical areas on the protein which determine activity.

Thus, the invention further includes variations of the BCSG1 polypeptide which show substantial BCSG1 polypeptide activity or which include regions of BCSG1 protein such as the protein portions discussed below. Such mutants include deletions, insertions, inversions, repeats, and type substitutions. As indicated above, guidance concerning which amino acid changes are likely to be phenotypically silent can be found in Bowie, J. U., et al., "Deciphering the Message in Protein Sequences: Tolerance to Amino Acid Substitutions," *Science* 247:1306–1310 (1990).

Thus, the fragment, derivative or analog of the polypeptide of FIG. 1 (SEQ ID NO:2), or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the polypeptide is fused with another compound, such as a compound to increase the half-life of the polypeptide (for example, polyethylene glycol), or (iv) one in which the additional amino acids are fused to the polypeptide, such as an IgG Fc fusion region peptide or leader or secretory sequence or a sequence which is employed for purification of the polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the BCSG1 protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)).

As indicated, changes are preferably of a minor nature, such as conservative amino acid substitutions that do not significantly affect the folding or activity of the protein (see Table 1).

TABLE 1

| Conservative Amino Acid Substitutions. | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on-many factors, including those described above. Generally speaking, the number of substitutions for any given AIM-II polypeptide will not be more than 50, 40, 30, 25, 20, 15, 10, 5 or 3.

Amino acids in the BCSG1 protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224: 899–904 (1992) and de Vos et al. *Science* 255:306–312 (1992)).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell or from a native source. For example, a recombinantly produced version of the BCSG1 polypeptide can be substantially purified by the one-step method described in Smith and Johnson, *Gene* 67:31–40 (1988).

The polypeptides of the present invention include the polypeptide encoded by the deposited cDNA; a polypeptide comprising amino acids about 1 to about 127 in SEQ ID NO:2 (FIG. 1); a polypeptide comprising amino acids about 2 to about 127 in SEQ ID NO:2; as well as polypeptides which are at least 80% identical, more preferably at least 90% or 95% identical, still more preferably at least 96%, 97%, 98% or 99% identical to the polypeptide encoded by the deposited cDNA, to the polypeptide of FIG. 1 (SEQ ID NO:2), and also include portions of such polypeptides with at least 30 amino acids and more preferably at least 50 amino acids.

By a polypeptide having an amino acid sequence at least, for example, 95% "identical" to a reference amino acid sequence of a BCSG1 polypeptide is intended that the amino acid sequence of the polypeptide is identical to the reference sequence except that the polypeptide sequence may include up to five amino acid alterations per each 100 amino acids of the reference amino acid of the BCSG1 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIG. 1 (SEQ ID NO:2) or to the amino acid sequence encoded by deposited cDNA clone can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art.

In another aspect, the invention provides a peptide or polypeptide comprising an epitope-bearing portion of a polypeptide of the invention. The epitope of this polypeptide portion is an immunogenic or antigenic epitope of a polypeptide described herein. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. *Science* 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767–778 (1984) at 777.

Antigenic epitope-bearing peptides and polypeptides of the invention preferably contain a sequence of at least seven, more preferably at least nine and most preferably between about at least about 15 to about 30 amino acids contained within the amino acid sequence of a polypeptide of the invention.

Non-limiting examples of antigenic polypeptides or peptides that can be used to generate BCSG1-specific antibodies include: a polypeptide comprising amino acid residues from about 94 to about 107 in FIG. 1 (SEQ ID NO:2); a polypeptide comprising amino acid residues from about 120 to about 127 in FIG. 1 (SEQ ID NO:2). As indicated above, the inventors have determined that the above polypeptide fragments are antigenic regions of the BCSG1 protein.

The epitope-bearing peptides and polypeptides of the invention may be produced by any conventional means. Houghten, R. A. (1985) General method for the rapid solid-phase synthesis of large numbers of peptides: specificity of antigen-antibody interaction at the level of individual amino acids. *Proc. Natl. Acad. Sci. USA*

82:5131–5135. This "Simultaneous Multiple Peptide Synthesis (SMPS)" process is further described in U.S. Pat. No. 4,631,211 to Houghten et al. (1986).

As one of skill in the art will appreciate, BCSG1 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84–86 (1988)). Fusion proteins that have a disulfide-linked dimeric structure due to the IgG part can also be more efficient in binding and neutralizing other molecules than the monomeric BCSG1 protein or protein fragment alone (Fountoulakis et al., *J. Biochem* 270:3958–3964 (1995)).

Cancer Diagnosis and Prognosis

There are two classes of genes affecting tumor development. Genes influencing the cancer phenotype that act directly as a result of changes (e.g., mutation) at the DNA level, such as BRCA1, BRCA2, and p53, are called Class I genes. The Class II genes affect the phenotype by modulation at the expression level. Development of breast cancer and subsequent malignant progression is associated with alterations of a variety of genes of both classes. Identification of quantitative changes in gene expression that occur in the malignant mammary gland, if sufficiently characterized, may yield novel molecular markers which may be useful in the diagnosis and treatment of human breast cancer.

The present inventors have identified a new breast cancer marker that is overexpressed in advanced infiltrating breast cancer cells. The lack of expression of BCSG1 in normal or benign breast epithelial cells and a weak expression in low grade in situ carcinomas suggest that overexpression of BCSG1 indicates breast cancer malignant progression. (See, Examples 6 and 7). It is unlikely that BCSG1 is overexpressed as a secondary effect of cellular proliferation because no detectable BCSG1 expression is evident in rapidly proliferating nonmalignant breast lesions. (See, Example 7).

BCSG1 may be useful in clinical management and treatment of breast cancer. In this regard, the expression of BCSG1 transcripts was observed in the neoplastic epithelial cells of infiltrating breast carcinoma but not in epithelial cells of normal and benign breast tissue. (See, Example 7). The overexpression of BCSG1 in malignant infiltrating breast epithelial cells compared to the low level expression in the low grade in situ carcinoma suggests that up-regulation of BCSG1 expression is associated with breast malignant progression and may signal the more advanced invasive/metastatic phenotype of human breast cancer. This implication is further supported by detection of BCSG1 expression in 4/4 breast cancer cell lines derived from ductal infiltrating carcinomas but not (0/3) in breast cancer cell lines derived from primary solid carcinoma (See, Example 6). BCSG1 overexpression in ductal carcinoma in situ (DCIS) may indicate a malignant progression leading to metastasis. There was a marked increase in DCIS incidence beginning in the early 1980s (Emster, V. L., et al., *JAMA* 275:913–918 (1996)). The total estimated number of DCIS cases in the United States in 1992 was 200% higher than expected based on 1983 rates and trends between 1973 and 1983 (Emster, V. L., et al., *JAMA* 275:913–918 (1996)).

While early detection of invasive breast cancer is beneficial, the value of DCIS detection is currently unknown. There is cause for concern about the large number of DCIS cases that are being diagnosed as a consequence of screening mammography, most of which are treated by some form of surgery. In addition, the proportion of cases treated by mastectomy may be inappropriately high (Emster, V. L., et al., *JAMA* 275:913–918 (1996)). BCSG1 expression may provide some prognostic information on distinguishing the DCIS which is not likely to become invasive from the DCIS which is most likely to become invasive, which will help to reduce some inappropriate or unnecessary mastectomies. In addition, the use of BCSG1 gene could be of great importance in differentiating atypical proliferative breast lesions from cancer and may be useful in screening of breast biopsies for potential abnormalities.

It is interesting to note that the predicted amino acid sequence of BCSG1 gene shares high sequence homology with the recently cloned non-Aβ component of Alzheimer's disease (AD) amyloid precursor protein (Ueda, K., et al., *Proc. Natl. Acad. Sci. USA*. 90 (23):11282–6 (1993)). A neuropathological hallmark of AD is a widespread amyloid deposition resulting from beta-amyloid precursor proteins (beta APPS). Beta APPs are large membrane-spanning proteins that either give rise to the beta A4 peptide (AB fragment) (Masters, C. L., et al., *Proc. Natl. Acad. Sci. USA* 82:4245–4249 (1985)) or a non-Aβ component of AD amyloid (Ueda, K., et al., *Proc. Natl. Acad. Sci. USA*. 90 (23):11282–6 (1993)) that is either deposited in AD amyloid plaques or yielding soluble forms. While the insoluble membrane-bound AD amyloid destabilizes calcium homeostasis and thus renders cell vulnerable to excitotoxic conditions of calcium influx resulting from energy deprivation or overexcitation (Mattson, M. P., et al., *Ann. N.Y. Acad. Sci.* 679:121 (1993)), the soluble AD amyloid proteins are neuroprotective against glucose deprivation and glutamate toxicity, perhaps through their ability to lower the intraneuronal calcium concentration (Barger, S. W., *J. Neurochem.* 64:2087–96 (1995)). It is possible that BCSG1, like soluble AD amyloid, may be potentially involved in tissue damage resulting from tissue remodeling due to the local cancer invasion. Nevertheless, Examples 6 and 7 demonstrate a stage-specific BCSG1 expression and an association of BCSG1 overexpression with clinical aggressiveness of breast cancers. BCSG1 overexpression may indicate breast cancer malignant progression from benign breast or low grade in situ carcinoma to the highly infiltrating carcinoma.

The Examples demonstrate that certain tissues in mammals with cancer express significantly enhanced levels of the BCSG1 protein and mRNA encoding the BCSG1 protein when compared to a corresponding "standard" mammal, i.e., a mammal of the same species not having the cancer. Further, it is believed that enhanced levels of the BCSG1 protein can be detected in certain body fluids (e.g., sera, plasma, urine, and spinal fluid) from mammals with cancer when compared to sera from mammals of the same species not having the cancer. Thus, the invention provides a diagnostic method useful during tumor diagnosis, which involves assaying the expression level of the gene encoding the BCSG1 protein in mammalian cells or body fluid and comparing the gene expression level with a standard BCSG1 gene expression level, whereby an increase in the gene expression level over the standard is indicative of certain tumors.

Where a tumor diagnosis has already been made according to conventional methods, the present invention is useful as a prognostic indicator, whereby patients exhibiting enhanced BCSG1 gene expression will experience a worse clinical outcome relative to patients expressing the gene at a lower level.

By "assaying the expression level of the gene encoding the BCSG1 protein" is intended qualitatively or quantitatively measuring or estimating the level of the BCSG1 protein or the level of the mRNA encoding the BCSG1 protein in a first biological sample either directly (e.g., by determining or estimating absolute protein level or mRNA level) or relatively (e.g., by comparing to the BCSG1 protein level or mRNA level in a second biological sample).

Preferably, the BCSG1 protein level or mRNA level in the first biological sample is measured or estimated and compared to a standard BCSG1 protein level or mRNA level, the standard being taken from a second biological sample obtained from an individual not having the cancer. As will be appreciated in the art, once a standard BCSG1 protein level or mRNA level is known, it can be used repeatedly as a standard for comparison.

By "biological sample" is intended any biological sample obtained from an individual, cell line, tissue culture, or other source which contains BCSG1 protein or mRNA. Biological samples include mammalian body fluids (such as sera, plasma, urine, synovial fluid and spinal fluid) which contain secreted mature BCSG1 protein, and ovarian, prostate, heart, placenta, pancreas liver, spleen, lung, breast and umbilical tissue.

The present invention is useful for detecting cancer in mammals. In particular the invention is useful during diagnosis of the of following types of cancers in mammals: breast, ovarian, prostate, bone, liver, lung, pancreatic, and spleenic. Preferred mammals include monkeys, apes, cats, dogs, cows, pigs, horses, rabbits and humans. Particularly preferred are humans.

Total cellular RNA can be isolated from a biological sample using the single-step guanidinium-thiocyanate-phenol-chloroform method described in Chomczynski and Sacchi, *Anal. Biochem.* 162:156–159 (1987). Levels of mRNA encoding the BCSG1 protein are then assayed using any appropriate method. These include Northern blot analysis (Harada et al., *Cell* 63:303–312 (1990)), S1 nuclease mapping (Fujita et al., *Cell* 49:357–367 (1987)), the polymerase chain reaction (PCR), reverse transcription in combination with the polymerase chain reaction (RT-PCR) (Makino et al., *Technique* 2:295–301 (1990)), and reverse transcription in combination with the ligase chain reaction (RT-LCR).

Assaying BCSG1 protein levels in a biological sample can occur using antibody-based techniques. For example, BCSG1 protein expression in tissues can be studied with classical immunohistological methods (Jalkanen, M., et al., *J. Cell. Biol.* 101:976–985 (1985); Jalkanen, M., et al., *J. Cell. Biol.* 105:3087–3096 (1987)).

Other antibody-based methods useful for detecting BCSG1 protein gene expression include immunoassays, such as the enzyme linked immunosorbent assay (ELISA) and the radioimmunoassay (RIA).

Suitable labels are known in the art and include enzyme labels, such as, Glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

Chromosome Assays

The nucleic acid molecules of the present invention are also valuable for chromosome identification. The sequence is specifically targeted to and can hybridize with a particular location on an individual human chromosome. The mapping of DNAs to chromosomes according to the present invention is an important first step in correlating those sequences with genes associated with disease.

In certain preferred embodiments in this regard, the cDNA herein disclosed is used to clone genomic DNA of a BCSG1 protein gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLES

Example 1

Expression and Purification of BCSG1 in *E. coli*

The bacterial expression vector pQE9 (pD10) is used for bacterial expression in this example. (QIAGEN, Inc., 9259 Eton Avenue, Chatsworth, Calif., 91311). pQE9 encodes ampicillin antibiotic resistance ("Amp"') and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that an inserted DNA fragment encoding a polypeptide expresses that polypeptide with the six His residues (i.e., a "6×His tag")) covalently linked to the amino terminus of that polypeptide.

The DNA sequence encoding the desired portion BCSG1 protein sequence is amplified from the deposited cDNA clone using PCR oligonucleotide primers which anneal to the amino terminal sequences of the desired portion of the BCSG1 protein and to sequences in the deposited construct 3' to the cDNA coding sequence. Additional nucleotides containing restriction sites to facilitate cloning in the pQE9 vector are added to the 5' and 3' primer sequences, respectively.

For cloning the mature protein, the 5' primer has the sequence 5' GGGGATCCATGTTTTCAAGAAGG 3' (SEQ ID NO:3) containing the underlined BamHI restriction site followed by 16 nucleotides complementary to the amino terminal coding sequence of the BCSG1 sequence in FIG. 1. One of ordinary skill in the art would appreciate, of course, that the point in the protein coding sequence where the 5' primer begins may be varied to amplify a DNA segment encoding any desired portion of the complete BCSG1 protein shorter or longer than the protein. The 3' primer has the sequence 5' GGAAGCTTCTAGTCTCCCCCACTCTGG 3' (SEQ ID NO:4) containing the underlined HindIII restriction site followed by 19 nucleotides complementary to the non-coding sequence of the BCSG1 DNA sequence in FIG. 1.

The amplified BCSG1 DNA fragment and the vector pQE9 are digested with BamHI/HindIII and the digested DNAs are then ligated together. Insertion of the BCSG1 DNA into the restricted pQE9 vector places the BCSG1 protein coding region downstream from the IPTG-inducible promoter and in-frame with an initiating AUG and the six histidine codons.

The ligation mixture is transformed into competent *E. coli* cells using standard procedures such as those described in Sambrook et al., *Molecular Cloning: a Laboratory Manual, 2nd Ed.*; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kan$^r$"), is used in carrying out the illustrative example described herein. This strain, which is only one of many that are suitable for expressing BCSG1 protein, is available commercially from QIAGEN, Inc., supra. Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 $\mu$g/ml) and kanamycin (25 $\mu$g/ml). The O/N culture is used to inoculate a large culture, at a dilution of approximately 1:25 to 1:250. The cells are grown to an optical density at 600 nm ("OD600") of between 0.4 and 0.6. Isopropyl-b-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4° C. in 6 M guanidine-HCl, pH 8. The cell debris is removed by centrifugation, and the supernatant containing the BCSG1 is loaded onto a nickel-nitrilo-tri-acetic acid ("NiNTA") affinity resin column (available from QIAGEN, Inc., supra). Proteins with a 6×His tag bind to the NI-NTA resin with high affinity and can be purified in a simple one-step procedure (for details see: The QIAexpressionist, 1995, QIAGEN, Inc., supra). Briefly the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the BCSG1 is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M–1M urea gradient in 500 mM NaCl, 20% glycerol, 20 mM Tris/HCl pH 7.4, containing protease inhibitors. The renaturation should be performed over a period of 1.5 hours or more. After renaturation the proteins can be eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

Example 2

Cloning and Expression of BCSG1 Protein in a Baculovirus Expression System

In this illustrative example, the plasmid shuttle vector pA2 GP is used to insert the cloned DNA encoding the protein into a baculovirus to express the BCSG1 protein, using a baculovirus leader and standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by the secretory signal peptide (leader) of the baculovirus gp67 protein and convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate viable virus that expresses the cloned polynucleotide.

Many other baculovirus vectors could be used in place of the vector above, such as pAc373, pVL941 and pAcIMI, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39.

The cDNA sequence encoding the BCSG1 protein in the deposited clone shown in FIG. 1 (SEQ ID NO:2), is amplified using PCR oligonucleotide primers corresponding to the 5' and 3' sequences of the gene.

The 5' primer has the sequence 5' GG GGATCCcGATGTTTTCAAGAAGG 3' (SEQ ID NO:5) (the lowercase "c" is a nucleotide included to preserve the coding frame) containing the underlined BamHI restriction enzyme site followed by 16 bases of the sequence of the BCSG1 protein shown in FIG. 1, beginning with the N-terminus of the protein. The 3' primer has the sequence 5'GG GGTACCCTAGTCTCCCCCACTCTGG 3' (SEQ ID NO:6) containing the underlined Asp718 restriction site followed by 18 nucleotides complementary to the 3' noncoding sequence in FIG. 1.

The amplified fragment is isolated from a 1% agarose gel using a commercially available kit ("Geneclean," BIO 101 Inc., La Jolla, Calif.). The fragment then is digested with BamHI/Asp718 and again is purified on a 1% agarose gel. This fragment is designated herein "F1".

The plasmid is digested with the restriction enzymes BamHI/Asp718 and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V1".

Fragment F1 and the dephosphorylated plasmid V1 are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria are identified that contain the plasmid with the human BCSG1 gene using the PCR method, in which one of the primers that is used to amplify the gene and the second primer is from well within the vector so that only those bacterial colonies containing the BCSG1 gene fragment will show amplification of the DNA. The sequence of the cloned fragment is confirmed by DNA sequencing. This plasmid is designated herein pBac BCSG1.

Five μg of the plasmid pBacBCSG1 is co-transfected with 1.0 μg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84:7413–7417 (1987). 1 μg of BaculoGold™ virus DNA and 5 μg of the plasmid pBac BCSG1 are mixed in a sterile well of a microtiter plate containing 50 μl of serum-free Grace's medium (Life Technologies Inc., Gaithersburg, Md.). Afterwards, 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10). After appropriate incubation, blue stained plaques are picked with the tip of a micropipettor (e.g., Eppendorf). The agar containing the recombinant viruses is then resuspended in a microcentrifuge tube containing 200 μl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-BCSG1.

To verify the expression of the BCSG1 gene, Sf9 cells are grown in Grace's medium supplemented with 10% heat inactivated FBS. The cells are infected with the recombinant baculovirus V-BCSG1 at a multiplicity of infection ("MOI") of about 2. Six hours later the medium is removed and is replaced with SF900 II medium minus methionine and cysteine (available from Life Technologies Inc., Rockville, Md.). If radiolabeled proteins are desired, 42 hours later, 5 μCi of $^{35}$S-methionine and 5 μCi $^{35}$S-cysteine (available from Amersham) are added. The cells are further incubated for 16 hours and then they are harvested by centrifugation. The proteins in the supernatant as well as the intracellular proteins are analyzed by SDS-PAGE followed by autoradiography (if radiolabeled). Microsequencing of the amino acid sequence of the amino terminus of purified protein may be used to determine the amino terminal sequence of the mature protein and thus the cleavage point and length of the secretory signal peptide.

Example 3

Cloning and Expression of BCSG1 in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLV I, HIV I and the early promoter of the cytomegalovirus (CMV). However, cellular elements can also be used (e.g., the human actin promoter). Suitable expression vectors for use in practicing the present invention include, for example, vectors such as PSVL and PMSG (Pharmacia, Uppsala, Sweden), pRSVcat (ATCC 37152), pSV2dhfr (ATCC 37146) and pBC12MI (ATCC 67109). Mammalian host cells that could be used include, human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS) (Murphy et al., *Biochem J.* 227:277–279 (1991); Bebbington et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., *Molecular and Cellular Biology*, 438–447 (March, 1985)) plus a fragment of the CMV-enhancer (Boshart et al., *Cell* 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 3(a)

Cloning and Expression in COS Cells

The expression plasmid, pBCSG1 HA, is made by cloning a cDNA encoding BCSG1 into the expression vector pcD-NAI/Amp or pcDNAIII (which can be obtained from Invitrogen, Inc.).

The expression vector pcDNAI/amp contains: (1) an E. coli origin of replication effective for propagation in E. coli and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., Cell 37:767 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding the BCSG1 is cloned into the polylinker region of the vector so that recombinant protein expression is directed by the CMV promoter. The plasmid construction strategy is as follows. The BCSG1 cDNA of the deposited clone is amplified using primers that contain convenient restriction sites, much as described above for construction of vectors for expression of BCSG1 in E. coli. Suitable primers include the following, which are used in this example. The 5' primer, containing the underlined BamHI site, a Kozak sequence, an AUG start codon and 4 codons of the 5' coding region of the complete BCSG1 has the following sequence: 5' GG GGATccgccaccATGTTTTCAAGAAGG 3' (SEQ ID NO:7) (Kozak sequence is represented by the lowercase letters). The 3' primer, containing the underlined BamHI site, a stop codon, and 19 bp of 3' coding sequence has the following sequence (at the 3' end): 5' GGGGATCCTCAgaaagcgt agtctgggacgtcgtatgggtaCTAGTCTCCCCCACTCT GG 3' (SEQ ID NO:8) (the HA tag is represented by the lowercase letters).

The PCR amplified DNA fragment and the vector, pcD-NAI/Amp, are digested with BamHI and then ligated. The ligation mixture is transformed into E. coli strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the BCSG1-encoding fragment.

For expression of recombinant BCSG1, COS cells are transfected with an expression vector, as described above, using DEAE-DEXTRAN, as described, for instance, in Sambrook et al., Molecular Cloning: a Laboratory Manual, Cold Spring Laboratory Press, Cold Spring Harbor, N.Y. (1989). Cells are incubated under conditions for expression of BCSG1 by the vector.

Expression of the BCSG1-HA fusion protein is detected by radiolabeling and immunoprecipitation, using methods described in, for example Harlow et al., Antibodies: A Laboratory Manual, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and lysed with detergent-containing RIPA buffer: 150 mM NaCl, 1% NP-40, 0.1% SDS, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b)

Cloning and Expression in CHO Cells

The vector pC4 is used for the expression of BCSG1 protein. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, J. Biol. Chem. 253:1357–1370, Hamlin, J. L. and Ma, C. 1990, Biochem. et Biophys. Acta, 1097:107–143, Page, M. J. and Sydenham, M. A. 1991, Biotechnology 9:64–68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rous Sarcoma Virus (Cullen, et al., Molecular and Cellular Biology, March 1985:438–447) plus a fragment isolated from the enhancer of the immediate early gene of human cytomegalovirus (CMV) (Boshart et al., Cell 41:521–530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the BCSG1 in a regulated way in mammalian cells (Gossen, M., & Bujard, H. 1992, Proc. Natl. Acad. Sci. USA 89: 5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes BamHI/Asp718 and then dephosphorylated using calf intestinal phosphatase by procedures known in the art. The vector is then isolated from a 1% agarose gel.

The DNA sequence encoding the BCSG1 protein sequence is amplified using PCR oligonucleotide primers corresponding to the 5' and 3' sequences of the gene. The 5' primer has the sequence 5' GG GGATccgccaccATGTTTTCAAGAAGG 3' (SEQ ID NO:7) (Kozak sequence is represented by the lowercase letters) containing the underlined BamHI restriction enzyme site followed by an efficient signal for initiation of translation in eukaryotes, as described by Kozak, M., *J. Mol. Biol.* 196: 947–950 (1987), and 15 bases of the coding sequence of BCSG1 shown in FIG. 1 (SEQ ID NO:1). The 3' primer has the sequence 5' GG GGTACCTCACTAGTCTCCCCCACTCTGG 3' (SEQ ID NO:9) containing the underlined Asp718 restriction site followed by 22 nucleotides complementary to the non-translated region of the BCSG1 gene shown in FIG. 1 (SEQ ID NO:1).

The amplified fragment is digested with the endonucleases BamHI/Asp718 and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. 5 µg of the expression plasmid pC4 is cotransfected with 0.5 µg of the plasmid pSV2-neo using lipofectin (Felgner et al., supra). The plasmid pSV2neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 µM, 2 µM, 5 µM, 10 mM, 20 mM). The same procedure is repeated until clones are obtained which grow at a concentration of 100–200 µM. Expression of the desired gene product is analyzed, for instance, by SDS-PAGE and Western blot or by reverse phase HPLC analysis.

Example 4

Tissue Distribution of BCSG1 mRNA Expression

Northern blot analysis was carried out to examine BCSG1 gene expression in human tissues as follows. Total RNA was extracted from tissues according to the method of Chomcznski and Sacchi (Chomczynski, P. & Sacchi, N., *Anal. Biochem.* 162:156–159 (1987)). Equal aliquots of RNA were electrophoresed in a 1.2% agarose gel containing formaldehyde and transferred to nylon membrane (Boehringer Mannheim). The membrane was pre-hybridized with ExpressHyb hybridization solution (Clontech, Inc.) at 68° C. for 30 min. The hybridization was carried out in the same solution with $^{32}$P-labeled BCSG1 probe (1.5×10$^6$ cpm/ml) for 1 hour at 68° C. The membrane was then rinsed in 2×SSC containing 0.05% SDS three times for 30 min at room temperature, followed by two washes with 0.1×SSC containing 0.1% SDS for 40 min at 50° C. The full-length BCSG1 cDNA (SEQ ID NO:1) was isolated from the Bluescript vector, following EcoRI and XhoI digestion, and used as a template for preparation of a random-labelled cDNA probe. Random primer DNA labeling kit was obtained from Boehringer Mannheim, Indianapolis. $^{32}$P-dATP was purchased from Amersham.

The northern blot showed that BCSG1 was abundantly expressed as the expected 1 kb transcript in brain which is a rich source for AD amyloid family genes. A much less intense band of similar size was also seen in the following tissues: ovary, testis, colon, and heart.

Example 5

Cloning of BCSG1 from cDNA Libraries

EST analysis was used to search for new genes differentially expressed in breast cancer versus normal breast. A data base containing approximately 500,000 human partial cDNA sequences (expressed sequence tags) has been established in a collaborative effort between the Institute for Genomic Research and Human Genome Science Inc., using high throughput automated DNA sequence analysis of randomly selected human cDNA clones (Adams, M. D., et al., *Science* 252:1651–6 (1991)). RNAs from a stage III breast carcinoma and patient-matched normal breast were isolated and subjected to preparation of cDNA libraries. EST automated DNA sequence analysis was performed on randomly selected cDNA clones. Both libraries had about 60% novel gene sequences which did not match exactly to published human genes. A total of 3048 ESTs from breast cancer cDNA library and 2886 ESTs from normal breast cDNA library were randomly picked and sequence analyzed. The ESTs with overlapping sequences were grouped into unique EST groups; and each EST group may represent a gene or a family of sequence-related genes. There were more than 2,200 EST groups that were analyzed for quantitative comparison of EST hits in the pair of cDNA libraries from normal breast versus breast cancer by examining the expression of individual EST sequences. The numbers of EST hits in the libraries reflect the relative expression or mRNA transcript copy numbers of the EST. This direct differential cDNA sequence, as illustrated in FIG. 2, utilizing the direct EST sequencing analysis simultaneously on a pair of cDNA libraries made from normal breast and breast cancer, was used to study expression profile of individual genes and patterns of genes in normal breast versus breast cancer.

Results cDNA libraries were generated from breast cancer biopsy specimen and patient-matched normal breast and were analyzed by EST sequencing. Approximately 6,000 ESTs were analyzed and grouped to different groups based on sequence overlapping, and 2,200 unique EST groups were first analyzed for relative expression in the cDNA libraries from normal breast versus breast cancer and then subjected to tissue-specific expression by examining tissue origins of individual EST sequences against a large population of ESTs derived from a variety of different tissue types. Three classes of EST groups were identified that were differentially expressed in normal breast versus breast cancer. As a demonstration of this approach, Table 1 shows a partial list of three classes of genes that are differentially expressed in normal breast versus breast cancer. Class I represents the genes more abundant in breast cancer than in normal breast and includes cathepsin D, a well-studied steroid regulated extracellular matrix-degrading proteinase (Rochefort, H., et al., *J. Cell. Biochem.* 35:17–29 (1987); Cavailles, V., et al., *Biochem. Biophys. Res. Commun.* 174:816–24 (1991); Capony, F. et al., *Biochem. Biophys. Res. Commun.* 171:972–80 (1990)). Cathepsin D is thought to play a role in breast cancer metastasis (Rochefort, H., et al., *J. Cell. Biochem.* 35:17–29 (1987); Cavailles, V., et al., *Biochem. Biophys. Res. Commun.* 174:816–24 (1991); Capony, F. et al., *Biochem. Biophys. Res. Commun.* 171:972–80 (1990)) and has been proposed as a prognostic marker in breast cancer progression (Brouillet, J. P., et al., *Eur. J. Cancer* 26:437–41 (1990); Spyratos, F., et al., *Lancet*, 11:1115–8 (1989); Rochefort, H., et al., *J. steroid. Biochem.* 34:177–82 (1989); Foekens J. A., et al., *JNCI* 87:751–6 (1995)). As listed, there were 5 cathepsin D ESTs sequenced in the breast cancer cDNA library and only 1 EST in the normal breast cDNA library. Another proposed breast cancer metastasis-related gene and a prognostic marker for breast cancer, 67 kDa laminin receptor (Horan-Hand, P., et al., *Cancer Res.* 45:833–40 (1986); Hunt, G. Exp. *Cell Biol* 57 (3):165–76 (1989); Castronovo, V., et al., *Am. J. Pathol.* 137 (6): 1373–81 (1990); Marques, L. A., et al., *Cancer Res.* 50 (5):1479–83 (1990); Gasparini, G., et al., *Int. J. Cancer.* 60 (5):604–10 (1995)), was also picked up in this class by the Differential cDNA Sequencing approach. Class II represents genes that are more abundant in normal breast than in breast cancer.

Although the genes in classes I and II are differentially expressed in normal breast versus breast cancer, none of these genes are unique to breast tissues. Class III is a special group of genes that are selectively expressed in breast relative to other tissue types. The tissue-specific expression of the unique gene was searched against approximately 500,000 ESTs using the BLAST program (Altschul, S. F., et al., *J. Mol. Biol.* 215 (3):403–10 (1990)). None of these breast cancer specific genes (BCSG) except the first one matched with any sequences in public gene sequence databases. BCSG1 was chosen for analysis as a first putative breast cancer maker gene because 1) its sequence has been matched with the sequence in public gene sequence database; and 2) most of the individual EST sequences in BCSG1 derived from a breast tumor cDNA library. Of the eight distinctive EST clones in BCSG1, seven of them were discovered in breast cDNA libraries and only one in a brain library. Of the seven EST clones discovered in the breast cDNA libraries, six of them were identified in the breast tumor library and only one in the normal breast library. After complete sequencing of all 6 EST clones, one EST clone was found to have a complete full-length sequence. The open reading frame of the resulting full-length gene is predicted to encode a 127 amino acid polypeptide. After optimal alignment, the putative BCSG1-encoded protein shows 54% sequence identity with the recently cloned non-Aβ fragment of human Alzheimer's disease (AD) amyloid protein (Ueda, K., et al., *Proc. Natl. Acad. Sci. USA.* 90 (23):11282–6 (1993)).

TABLE 1

PARTIAL LIST OF DIFFERENTIAL EXPRESSED GENES IN NORMAL VERSUS CANCEROUS BREAST IDENTIFIED BY DIFFERENTIAL cDNA SEQUENCING

| Genes | EST | |
|---|---|---|
| | Cancer | Normal |
| Genes more abundant in breast cancer | | |
| Breast basic conserved gene | 33 | 9 |
| Cathepsin D | 5 | 1 |
| 67 kDa laminin Receptor | 4 | 0 |
| Elongation factor 1 | 13 | 5 |
| Genes More Abundant in Normal Breast | | |
| Matrix Gla protein | 0 | 8 |
| 23 kDa Highly basic Protein | 3 | 11 |

| Genes | EST | | |
|---|---|---|---|
| | NB[1] | BC[2] | All Tissues |
| Genes as Breast-Specific and Differentially Expressed | | | |
| BCSG1 | 1 | 6 | 8 |
| BCSG2 | 0 | 7 | 7 |
| BCSG3 | 0 | 5 | 5 |
| BCSG4 | 4 | 0 | 4 |
| BCSG5 | 0 | 4 | 4 |

[1] normal breast;
[2] breast cancer

Table 1. Complementary DNA libraries were established from a stage III breast carcinoma and patient-matched normal breast. A total of 5,934 ESTs were randomly picked and sequence analyzed. More than 2,200 distinctive EST groups were analyzed for quantitative comparison of EST hits in the pair of cDNA libraries from breast cancer versus normal breast as described in "Materials and Methods". The same EST groups were also analyzed by examining the tissue-specific expression against the total of 500,000 ESTs from a variety of different cDNA libraries. Only a unique EST group with more than 3 breast-specific EST hits was listed and the rest of the several dozens EST groups with fewer than 4 breast-specific EST hits were omitted in this list.

Example 6

Expression of BCSG1 in Human Breast Cancer Cells

In an attempt to evaluate the potential biological significance of BCSG1 on human breast cancer development and progression, BCSG1 gene expression in human breast biopsy samples was examined using Northern blot analysis.

The RNA from human breast cancer cells was prepared using the RNA isolation kit RNAzol B (Tel-Test, Inc) based on the manufacturer's instruction. Equal aliquots of RNA were electrophoresed in a 1.2% agarose gel containing formaldehyde and transferred to nylon membrane (Boehringer Mannheim). The membrane was pre-hybridized with ExpressHyb hybridization solution (Clontech, Inc.) at 68° C. for 30 min. The hybridization was carried out in the same solution with $^{32}$P-labeled BCSG1 probe ($1.5 \times 10^6$ cpm/ml) for 1 hour at 68° C. The membrane was then rinsed in 2×SSC containing 0.05% SDS three times for 30 min at room temperature, followed by two washes with 0.1×SSC containing 0.1% SDS for 40 min at 50° C. The full-length BCSG1 cDNA (SEQ ID NO:1) was isolated from the Bluescript vector, following EcoRI and XhoI digestion, and used as a template for preparation of a random-labelled cDNA probe. Random primer DNA labeling kit was obtained from Boehringer Mannheim, Indianapolis. $^{32}$P-dATP was purchased from Amersham.

The expression of BCSG1 in metastatic breast carcinoma and benign breast tissue were analyzed by Northern blotting. Overexpression of the BCSG1 transcript in breast carcinoma. In contrast, the BCSG1 transcript was undetectable in benign breast tissue. The presence of BCSG1 transcript in human breast tissue and its overexpression in breast carcinomas are consistent with the differential cDNA sequencing cloning strategy which suggests a possible role or a biomarker of up-regulation of BCSG1 in the development of breast cancer.

The expression of BCSG1 was also examined in a variety of human breast cancer cell lines, namely, primary solid tumor derived cell lines H3477, H3630, H3680B; pleural effusion derived cell lines H3396, MCF7, SKBR-3 MDAMB231; infiltrating ductal carcinoma derived cell lines H3914, H3922, ZR- 75-1, T47D. Cell lines of T47D, ZR-75-1, SKBR-3, MCF-7 and MDA-MB-231 are from ATCC; all other lines were initially isolated at Bristol-Myers Squibb Pharmaceutical Research Institute (Liu, J., *Cancer Res.*).

Northern blot detected the 1 Kb BCSG1 transcript in 2 of the 4 cell lines derived from pleural effusion (i.e., SKBR-3 MDAMB231) and all 4 cell lines detected from ductal infiltrating carcinomas. Interestingly, none of the cell lines derived from primary solid breast carcinoma expressed BCSG1 mRNA. Among these lines, H3922 expressed the highest level of BCSG1 mRNA. The absence of BCSG1 mRNA in some pleural effusion derived cell lines suggest that the expression of BCSG1 gene may require specific in vivo conditions, or that it is induced by interactions between the tumor cells and stromal cells.

Example 7

In Situ Hybridization of BCSG1 in Breast Cancer Cells

In order to localize the cellular source of the BCSG1 expression and to further assess the biological relevance of the overexpression of BCSG1 in breast cancers, in situ hybridization was performed on fixed breast sections from 20 infiltrating carcinomas, 15 in situ carcinomas, and 15 benign breast lesions (breast hyperplasia and fibroadenoma).

In situ hybridization was carried out as described (M. L. Angerer & R. C. Angerer, In: *In situ hybridization*, D. Rickwood and B. D. Hames (ed.). London: LRL Press., (1992), pp. 15–32). Briefly, deparaffinized and acid-treated sections (5-um thick) were treated with proteinase K, prehybridized, and hybridized overnight with digoxigenin labeled anti-sense transcripts from a BCSG1 cDNA insert. The BCSG1 antisense probe is a 550 bp full-length fragment. The probe was generated by PstI cut of BCSG1 cDNA plasmid and followed by T7 polymerase. Hybridization was followed by RNase treatment and three stringent washings. Sections were incubated with mouse anti-digoxigenin antibodies (Boehringer) followed by the incubation with biotin-conjugated secondary rabbit anti-mouse antibodies (DAKO). The calorimetric detection were performed using a standard indirect streptavidin-biotin immunoreaction method by DAKO's Universal LSAB Kit according to manufacturer's instructions.

In these experiments, two aspects of BCSG1 expression were examined: 1) the tissue localization (stromal versus epithelial); and 2) the correlation of BCSG1 expression and breast cancer malignant phenotype. A strongly positive BCSG1 hybridization in neoplastic epithelial cells of highly infiltrating breast carcinomas was observed. The expression of BCSG1 mRNA was detectable in the neoplastic epithelial cells in 18 of 20 infiltrating breast carcinomas. No expression of BCSG1 was detected in the stromal cells. In contrast, expression of BCSG1 was absent in all 15 cases of normal or benign breast lesions. A representative negative staining of BCSG1 in an atypical proliferative breast lesion, a benign fibroadenoma, and normal ductal breast epithelial cells are presented. Furthermore, in a highly invasive breast carcinoma, no detectable signal of BCSG1 expression was evident in the residual normal lobular breast epithelial cells although the surrounding invasive breast carcinoma cells were stained positive for BCSG1 expression. These in situ hybridization results are consistent with the Northern blot analysis which showed a strong expression of BCSG1 transcript in breast carcinoma but not in normal or benign breast lesions.

It is interesting to note that although a strong BCSG1 signal was easily detected in the malignant breast epithelial cells of infiltrating breast carcinoma, the low grade in situ carcinomas showed a sparse and a light staining. Among 15 in situ carcinomas, 9 specimens were stained negatively and 6 specimens were partially stained. Both the intensity of staining and the number of positive cells were significantly reduced in the in situ breast carcinomas compared to the strong expression in the metastatic breast carcinomas. These results, which demonstrated a gradient and stage-specific BCSG1 expression from virtually no detectable expression in normal or benign breast to the low level and partial expression in the low grade in situ breast carcinoma and to the high expression in the infiltrating malignant breast carcinomas, suggest an association of BCSG1 expression with breast cancer malignant progression. Based on this BCSG1 expression pattern, BCSG1 is useful as a breast cancer progression marker.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. An isolated polynucleotide comprising a nucleic acid encoding amino acids 2 to 127 of SEQ ID NO:2.

2. The isolated polynucleotide of claim 1, comprising nucleotide 15 to 392 of SEQ ID NO:1.

3. The isolated polynucleotide of claim 1, comprising a nucleic acid encoding amino acids 1 to 127 of SEQ ID NO:2.

4. The isolated polynucleotide of claim 3, comprising nucleotide 12 to 392 of SEQ ID NO:1.

5. The isolated polynucleotide of claim 1, which is DNA.

6. The isolated polynucleotide of claim 1, which is RNA.

7. The isolated polynucleotide of claim 1, further comprising a heterologous polynucleotide.

8. The isolated polynucleotide of claim 7, wherein said heterologous polynucleotide encodes a heterologous polypeptide.

9. A method of producing a vector that comprises inserting the isolated polynucleotide of claim 1 into a vector.

10. A vector comprising the isolated polynucleotide of claim 1.

11. The vector of claim 10, wherein said polynucleotide is operably associated with a heterologous regulatory sequence.

12. An isolated host cell comprising the isolated polynucleotide of claim 1.

13. The host cell of claim 12, wherein said isolated polynucleotide is operably associated with a heterologous regulatory sequence.

14. A method of producing a polypeptide that comprises culturing the host cell of claim 13 under conditions such that said polypeptide is expressed, and recovering said polypeptide.

15. A composition comprising the isolated polynucleotide of claim 1 and a pharmaceutically acceptable carrier.

16. An isolated polynucleotide comprising a nucleic acid encoding the complete amino acid sequence encoded by the cDNA clone of ATCC Deposit No. 97856.

17. The isolated polynucleotide of claim 16, which is DNA.

18. The isolated polynucleotide of claim 16, which is RNA.

19. The isolated polynucleotide of claim 16, further comprising a heterologous polynucleotide.

20. The isolated polynucleotide of claim 19, wherein said heterologous polynucleotide encodes a heterologous polypeptide.

21. A method of producing a vector that comprises inserting the isolated polynucleotide of claim 16 into a vector.

22. A vector comprising the isolated polynucleotide of claim 16.

23. The vector of claim 22, wherein said polynucleotide is operably associated with a heterologous regulatory sequence.

24. An isolated host cell comprising the isolated polynucleotide of claim 16.

25. The host cell of claim 24, wherein said isolated polynucleotide is operably associated with a heterologous regulatory sequence.

26. A method of producing a polypeptide that comprises culturing the host cell of claim 25 under conditions such that said polypeptide is expressed, and recovering said polypeptide.

27. A composition comprising the isolated polypeptide of claim 16 and a pharmaceutically acceptable carrier.

28. An isolated polynucleotide fragment of SEQ ID NO:1 consisting of at least 100 contiguous nucleotides of the coding region of SEQ ID NO:1 or the complete complement thereof.

29. The isolated polynucleotide fragment of claim 28, consisting of at least 250 contiguous nucleotides of the coding region of SEQ ID NO:1 or the complement thereof.

30. The isolated polynucleotide of claim 28, which is DNA.

31. The isolated polynucleotide of claim 28, which is RNA.

32. A method of producing a vector that comprises inserting the isolated polynucleotide of claim 28 into a vector.

33. A vector comprising the isolated polynucleotide of claim 28.

34. An isolated host cell comprising the isolated polynucleotide of claim 28.

35. An isolated polynucleotide, encoding a fragment of SEQ ID NO:2 selected from the group consisting of:
   (a) a polypeptide consisting of at least amino acids 94 to 107 of SEQ ID NO:2; and
   (b) a polypeptide consisting of at least amino acids 120 to 127 of SEQ ID NO:2.

36. The isolated polynucleotide of claim 35, wherein said polypeptide is (a).

37. The isolated polynucleotide of claim 35, wherein said polypeptide is (b).

38. The isolated polynucleotide of claim 35, which is DNA.

39. The isolated polynucleotide of claim 35, which is RNA.

40. The isolated polynucleotide of claim 35, further comprising a heterologous polynucleotide.

41. The isolated polynucleotide of claim 40, wherein said heterologous polynucleotide encodes a heterologous polypeptide.

42. A method of producing a vector that comprises inserting the isolated polynucleotide of claim 35 into a vector.

43. A vector comprising the isolated polynucleotide of claim 35.

44. The vector of claim 43, wherein said polynucleotide is operably associated with a heterologous regulatory sequence.

45. An isolated host cell comprising the isolated polynucleotide of claim 33.

46. The host cell of claim 45, wherein said isolated polynucleotide is operably associated with a heterologous regulatory sequence.

47. A method of producing a polypeptide that comprises culturing the host cell of claim 46 under conditions such that said polypeptide is expressed, and recovering said polypeptide.

48. A composition comprising the isolated polynucleotide of claim 35 and a pharmaceutically acceptable carrier.

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 550 base pairs
      (B) TYPE: nucleic acid
      (C) STRANDEDNESS: double
      (D) TOPOLOGY: both (ii) MOLECULE TYPE: cDNA (ix) FEATURE:
      (A) NAME/KEY: CDS
      (B) LOCATION: 12..392

(xi) SEQUENCE DESCRIPTION: SEQ ID NO:1:

```
CACGAGCCAC C ATG GAT GTT TTC AAG AAG GGC TTC TCC ATC GCC AAG AAG      50
             Met Asp Val Phe Lys Lys Gly Phe Ser Ile Ala Lys Lys
               1               5                  10

GGC GTG GTG GGT GCG GTG GAA AAG ACC AAG CAG GGG GTG ACG GAA GCA      98
Gly Val Val Gly Ala Val Glu Lys Thr Lys Gln Gly Val Thr Glu Ala
     15                  20                  25

GCT GAG AAG ACC AAG GAG GGG GTC ATG TAT GTG GGA GCC AAG ACC AAG     146
Ala Glu Lys Thr Lys Glu Gly Val Met Tyr Val Gly Ala Lys Thr Lys
 30                  35                  40                  45

GAG AAT GTT GTA CAG AGC GTG ACC TCA GTG GCC GAG AAG ACC AAG GAG     194
Glu Asn Val Val Gln Ser Val Thr Ser Val Ala Glu Lys Thr Lys Glu
                 50                  55                  60

CAG GCC AAC GCC GTG AGC AAG GCT GTG GTG AGC AGC GTC AAC ACT GTG     242
Gln Ala Asn Ala Val Ser Lys Ala Val Val Ser Ser Val Asn Thr Val
             65                  70                  75

GCC ACC AAG ACC GTG GAG GAG GCG GAG AAC ATC GCG GTC ACC TCC GGG     290
Ala Thr Lys Thr Val Glu Glu Ala Glu Asn Ile Ala Val Thr Ser Gly
         80                  85                  90

GTG GTG CGC AAG GAG GAC TTG AGG CCA TCT GCC CCC CAA CAG GAG GGT     338
Val Val Arg Lys Glu Asp Leu Arg Pro Ser Ala Pro Gln Gln Glu Gly
     95                 100                 105

GAG GCA TCC AAA GAG AAA GAG GAA GTG GCA GAG GAG GCC CAG AGT GGG     386
Glu Ala Ser Lys Glu Lys Glu Glu Val Ala Glu Glu Ala Gln Ser Gly
110                 115                 120                 125

GGA GAC TAGAGGGCTA CAGGCCAGCG TGGATGACCT GAAGAGCGCT CCTCTGCCTT      442
Gly Asp

GGACACCATC CCCTCCTAGC ACAAGGAGTG CCCGCCTTGA GTGACATGCG GGTGCCCACG     502

CTCCTGCCCT CGTCTCCCTG GACACCCTTG GCCTGTCCAC CTGTGCTG                550
```

(2) INFORMATION FOR SEQ ID NO:2:

(i) SEQUENCE CHARACTERISTICS:
      (A) LENGTH: 127 amino acids
      (B) TYPE: amino acid
      (D) TOPOLOGY: linear (ii) MOLECULE TYPE: protein (xi) SEQUENCE DESCRIPTION: SEQ ID NO:2:

```
Met Asp Val Phe Lys Lys Gly Phe Ser Ile Ala Lys Lys Gly Val Val
  1               5                  10                  15

Gly Ala Val Glu Lys Thr Lys Gln Gly Val Thr Glu Ala Ala Glu Lys
```

```
                  20                  25                  30

Thr Lys Glu Gly Val Met Tyr Val Gly Ala Lys Thr Lys Glu Asn Val
        35                  40                  45

Val Gln Ser Val Thr Ser Val Ala Glu Lys Thr Lys Glu Gln Ala Asn
    50                  55                  60

Ala Val Ser Lys Ala Val Val Ser Ser Val Asn Thr Val Ala Thr Lys
65                  70                  75                  80

Thr Val Glu Glu Ala Glu Asn Ile Ala Val Thr Ser Gly Val Val Arg
                85                  90                  95

Lys Glu Asp Leu Arg Pro Ser Ala Pro Gln Gln Glu Gly Glu Ala Ser
            100                 105                 110

Lys Glu Lys Glu Glu Val Ala Glu Glu Ala Gln Ser Gly Gly Asp
        115                 120                 125
```

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
GGGGATCCAT GTTTTCAAGA AGG                                             23
```

(2) INFORMATION FOR SEQ ID NO:4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
GGAAGCTTCT AGTCTCCCCC ACTCTGG                                         27
```

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
GGGGATCCCG ATGTTTTCAA GAAGG                                           25
```

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
GGGGTACCCT AGTCTCCCCC ACTCTGG                                         27
```

(2) INFORMATION FOR SEQ ID NO:7:

(i) SEQUENCE CHARACTERISTICS:
    (A) LENGTH: 29 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:7:

GGGGATCCGC CACCATGTTT TCAAGAAGG                                    29

(2) INFORMATION FOR SEQ ID NO:8:

(i) SEQUENCE CHARACTERISTICS:
    (A) LENGTH: 60 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:8:

GGGGATCCTC AGAAAGCGTA GTCTGGGACG TCGTATGGGT ACTAGTCTCC CCCACTCTGG   60

(2) INFORMATION FOR SEQ ID NO:9:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:9:

GGGGTACCTC ACTAGTCTCC CCCACTCTGG                                   30

(2) INFORMATION FOR SEQ ID NO:10:

(i) SEQUENCE CHARACTERISTICS:
    (A) LENGTH: 3974 base pairs
    (B) TYPE: nucleic acid
    (C) STRANDEDNESS: both
    (D) TOPOLOGY: both (ii) MOLECULE TYPE: cDNA (xi) SEQUENCE DESCRIPTION: SEQ ID NO:10:

GGTACCTAAG TGAGTAGGGC GTCCGATCGA CGGACGCCTT TTTTTTGAAT TCGTAATCAT    60

GGTCATAGCT GTTTCCTGTG TGAAATTGTT ATCCGCTCAC AATTCCACAC AACATACGAG   120

CCGGAAGCAT AAAGTGTAAA GCCTGGGGTG CCTAATGAGT GAGCTAACTC ACATTAATTG   180

CGTTGCGCTC ACTGCCCGCT TTCCAGTCGG GAAACCTGTC GTGCCAGCTG CATTAATGAA   240

TCGGCCAACG CGCGGGGAGA GGCGGTTTGC GTATTGGGCG CTCTTCCGCT TCCTCGCTCA   300

CTGACTCGCT GCGCTCGGTC GTTCGGCTGC GGCGAGCGGT ATCAGCTCAC TCAAAGGCGG   360

TAATACGGTT ATCCACAGAA TCAGGGGATA ACGCAGGAAA GAACATGTGA GCAAAAGGCC   420

AGCAAAAGGC CAGGAACCGT AAAAAGGCCG CGTTGCTGGC GTTTTTCCAT AGGCTCCGCC   480

CCCCTGACGA GCATCACAAA AATCGACGCT CAAGTCAGAG GTGGCGAAAC CCGACAGGAC   540

TATAAAGATA CCAGGCGTTT CCCCCTGGAA GCTCCCTCGT GCGCTCTCCT GTTCCGACCC   600

-continued

| | | | | | |
|---|---|---|---|---|---|
| TGCCGCTTAC | CGGATACCTG | TCCGCCTTTC | TCCCTTCGGG | AAGCGTGGCG | CTTTCTCATA | 660 |
| GCTCACGCTG | TAGGTATCTC | AGTTCGGTGT | AGGTCGTTCG | CTCCAAGCTG | GGCTGTGTGC | 720 |
| ACGAACCCCC | CGTTCAGCCC | GACCGCTGCG | CCTTATCCGG | TAACTATCGT | CTTGAGTCCA | 780 |
| ACCCGGTAAG | ACACGACTTA | TCGCCACTGG | CAGCAGCCAC | TGGTAACAGG | ATTAGCAGAG | 840 |
| CGAGGTATGT | AGGCGGTGCT | ACAGAGTTCT | TGAAGTGGTG | GCCTAACTAC | GGCTACACTA | 900 |
| GAAGAACAGT | ATTTGGTATC | TGCGCTCTGC | TGAAGCCAGT | TACCTTCGGA | AAAAGAGTTG | 960 |
| GTAGCTCTTG | ATCCGGCAAA | CAAACCACCG | CTGGTAGCGG | TGGTTTTTTT | GTTTGCAAGC | 1020 |
| AGCAGATTAC | GCGCAGAAAA | AAAGGATCTC | AAGAAGATCC | TTTGATCTTT | TCTACGGGGT | 1080 |
| CTGACGCTCA | GTGGAACGAA | AACTCACGTT | AAGGGATTTT | GGTCATGAGA | TTATCGTCGA | 1140 |
| CAATTCGCGC | GCGAAGGCGA | AGCGGCATGC | ATTTACGTTG | ACACCATCGA | ATGGTGCAAA | 1200 |
| ACCTTTCGCG | GTATGGCATG | ATAGCGCCCG | GAAGAGAGTC | AATTCAGGGT | GGTGAATGTG | 1260 |
| AAACCAGTAA | CGTTATACGA | TGTCGCAGAG | TATGCCGGTG | TCTCTTATCA | GACCGTTTCC | 1320 |
| CGCGTGGTGA | ACCAGGCCAG | CCACGTTTCT | GCGAAAACGC | GGGAAAAAGT | GGAAGCGGCG | 1380 |
| ATGGCGGAGC | TGAATTACAT | TCCCAACCGC | GTGGCACAAC | AACTGGCGGG | CAAACAGTCG | 1440 |
| TTGCTGATTG | GCGTTGCCAC | CTCCAGTCTG | GCCCTGCACG | CGCCGTCGCA | AATTGTCGCG | 1500 |
| GCGATTAAAT | CTCGCGCCGA | TCAACTGGGT | GCCAGCGTGG | TGGTGTCGAT | GGTAGAACGA | 1560 |
| AGCGGCGTCG | AAGCCTGTAA | AGCGGCGGTG | CACAATCTTC | TCGCGCAACG | CGTCAGTGGG | 1620 |
| CTGATCATTA | ACTATCCGCT | GGATGACCAG | GATGCCATTG | CTGTGGAAGC | TGCCTGCACT | 1680 |
| AATGTTCCGG | CGTTATTTCT | TGATGTCTCT | GACCAGACAC | CCATCAACAG | TATTATTTTC | 1740 |
| TCCCATGAAG | ACGGTACGCG | ACTGGGCGTG | GAGCATCTGG | TCGCATTGGG | TCACCAGCAA | 1800 |
| ATCGCGCTGT | TAGCGGGCCC | ATTAAGTTCT | GTCTCGGCGC | GTCTGCGTCT | GGCTGGCTGG | 1860 |
| CATAAATATC | TCACTCGCAA | TCAAATTCAG | CCGATAGCGG | AACGGGAAGG | CGACTGGAGT | 1920 |
| GCCATGTCCG | GTTTTCAACA | AACCATGCAA | ATGCTGAATG | AGGGCATCGT | TCCCACTGCG | 1980 |
| ATGCTGGTTG | CCAACGATCA | GATGGCGCTG | GGCGCAATGC | GCGCCATTAC | CGAGTCCGGG | 2040 |
| CTGCGCGTTG | GTGCGGATAT | CTCGGTAGTG | GGATACGACG | ATACCGAAGA | CAGCTCATGT | 2100 |
| TATATCCCGC | CGTTAACCAC | CATCAAACAG | GATTTTCGCC | TGCTGGGGCA | AACCAGCGTG | 2160 |
| GACCGCTTGC | TGCAACTCTC | TCAGGGCCAG | GCGGTGAAGG | GCAATCAGCT | GTTGCCCGTC | 2220 |
| TCACTGGTGA | AAAGAAAAAC | CACCCTGGCG | CCCAATACGC | AAACCGCCTC | TCCCCGCGCG | 2280 |
| TTGGCCGATT | CATTAATGCA | GCTGGCACGA | CAGGTTTCCC | GACTGGAAAG | CGGGCAGTGA | 2340 |
| GCGCAACGCA | ATTAATGTAA | GTTAGCGCGA | ATTGTCGACC | AAAGCGGCCA | TCGTGCCTCC | 2400 |
| CCACTCCTGC | AGTTCGGGGG | CATGGATGCG | CGGATAGCCG | CTGCTGGTTT | CCTGGATGCC | 2460 |
| GACGGATTTG | CACTGCCGGT | AGAACTCCGC | GAGGTCGTCC | AGCCTCAGGC | AGCAGCTGAA | 2520 |
| CCAACTCGCG | AGGGGATCGA | GCCCGGGGTG | GGCGAAGAAC | TCCAGCATGA | GATCCCCGCG | 2580 |
| CTGGAGGATC | ATCCAGCCGG | CGTCCCGGAA | AACGATTCCG | AAGCCCAACC | TTTCATAGAA | 2640 |
| GGCGGCGGTG | GAATCGAAAT | CTCGTGATGG | CAGGTTGGGC | GTCGCTTGGT | CGGTCATTTC | 2700 |
| GAACCCCAGA | GTCCCGCTCA | GAAGAACTCG | TCAAGAAGGC | GATAGAAGGC | GATGCGCTGC | 2760 |
| GAATCGGGAG | CGGCGATACC | GTAAAGCACG | AGGAAGCGGT | CAGCCCATTC | GCCGCCAAGC | 2820 |
| TCTTCAGCAA | TATCACGGGT | AGCCAACGCT | ATGTCCTGAT | AGCGGTCCGC | CACACCCAGC | 2880 |
| CGGCCACAGT | CGATGAATCC | AGAAAAGCGG | CCATTTTCCA | CCATGATATT | CGGCAAGCAG | 2940 |
| GCATCGCCAT | GGGTCACGAC | GAGATCCTCG | CCGTCGGGCA | TGCGCGCCTT | GAGCCTGGCG | 3000 |

```
AACAGTTCGG CTGGCGCGAG CCCCTGATGC TCTTCGTCCA GATCATCCTG ATCGACAAGA      3060

CCGGCTTCCA TCCGAGTACG TGCTCGCTCG ATGCGATGTT TCGCTTGGTG GTCGAATGGG      3120

CAGGTAGCCG GATCAAGCGT ATGCAGCCGC CGCATTGCAT CAGCCATGAT GGATACTTTC      3180

TCGGCAGGAG CAAGGTGAGA TGACAGGAGA TCCTGCCCCG GCACTTCGCC AATAGCAGC       3240

CAGTCCCTTC CCGCTTCAGT GACAACGTCG AGCACAGCTG CGCAAGGAAC GCCCGTCGTG      3300

GCCAGCCACG ATAGCCGCGC TGCCTCGTCC TGCAGTTCAT TCAGGGCACC GGACAGGTCG      3360

GTCTTGACAA AAAGAACCGG GCGCCCCTGC GCTGACAGCC GGAACACGGC GGCATCAGAG      3420

CAGCCGATTG TCTGTTGTGC CCAGTCATAG CCGAATAGCC TCTCCACCCA AGCGGCCGGA      3480

GAACCTGCGT GCAATCCATC TTGTTCAATC ATGCGAAACG ATCCTCATCC TGTCTCTTGA      3540

TCAGATCTTG ATCCCCTGCG CCATCAGATC CTTGGCGGCA AGAAAGCCAT CCAGTTTACT      3600

TTGCAGGGCT TCCCAACCTT ACCAGAGGGC GCCCCAGCTG GCAATTCCGG TTCGCTTGCT      3660

GTCCATAAAA CCGCCCAGTC TAGCTATCGC CATGTAAGCC CACTGCAAGC TACCTGCTTT      3720

CTCTTTGCGC TTGCGTTTTC CCTTGTCCAG ATAGCCCAGT AGCTGACATT CATCCGGGGT      3780

CAGCACCGTT TCTGCGGACT GGCTTTCTAC GTGTTCCGCT TCCTTTAGCA GCCCTTGCGC      3840

CCTGAGTGCT TGCGGCAGCG TGAAGCTTAA AAAACTGCAA AAAATAGTTT GACTTGTGAG      3900

CGGATAACAA TTAAGATGTA CCCAATTGTG AGCGGATAAC AATTTCACAC ATTAAAGAGG      3960

AGAAATTACA TATG                                                       3974

(2) INFORMATION FOR SEQ ID NO:11:

(i) SEQUENCE CHARACTERISTICS:
        (A) LENGTH: 112 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:11:

AAGCTTAAAA AACTGCAAAA AATAGTTTGA CTTGTGAGCG GATAACAATT AAGATGTACC       60

CAATTGTGAG CGGATAACAA TTTCACACAT TAAAGAGGAG AAATTACATA TG             112

(2) INFORMATION FOR SEQ ID NO:12:

(i) SEQUENCE CHARACTERISTICS:
        (A) LENGTH: 755 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:12:

GCCGCTGCGG CAGACTCGAG CCAGCTCAAG CCCGCAGCTC GCAGGGAGAT CCAGCTCCGT       60

CCTGCCTGCA GCAGCCAACC CTGCACACCC ACCATGGATG TTTCAAGAAG GCTTCTCCA      120

TCGCCAAGGA GGGCGTGGTG GGTGCGGTGG AAAAGACCAA GCAGGGGGTG ACGGAAGCAG     180

CTGAGAAGAC CAAGGAGGGG GTCATGTATG TGGGAGCCAA GACCAAGGAG AATGTTGTAT     240

GTACAGAGCG TGACCTCAGT GGCCGAGAAG ACCAAGGAGC AGGCCAACGC CGTGAGCAAG     300

GCTGTGGTGA GCAGCGTCAA CACTTGGCCA CCAAGACCGT GAGGAGGCGG AGAACATCGC     360

GGTCACTCCG GGTGTGCGCA AGGAGGATTA GGCCATTCCC CCCAACAGGA GGGTGAGGCA     420
```

-continued

| | | | | | |
|---|---|---|---|---|---|
| TCAAGAAGAG | AAGGGCAGGC | AGAGTGGGGG | AGACTAGAGG | GCTACAGGCC | AGCTTGGATG | 480 |
| ACCTGAAGAG | CGCTCCTCTG | CCTTGGGACA | CCATCCCCTC | CTAGCACAAG | GAGTGCCCGC | 540 |
| TTTGAGTGGA | CATGCGGCTG | TCCCACGTTC | CTGCCCTCGT | TTTCCCTGGG | CCACCTTGGC | 600 |
| CTGTCCAACT | GTGCTGTTGC | AACCAACTTA | ATTGCCTTCC | TTGGGCCCCA | ACCAACTTTT | 660 |
| TGGTTCTTTT | TGACCCATTT | ATGTTTGTTG | TGAATTTTTT | TTTTAAAAGA | TTTCAAATAA | 720 |
| AATTTGGGCC | CATTTTTTAA | AAAAAAAAAA | AAAAA | | | 755 |